United States Patent
Baxter et al.

(10) Patent No.: US 6,566,376 B1
(45) Date of Patent: May 20, 2003

(54) DIPHENYL-PIPERIDINE DERIVATIVE

(75) Inventors: Andrew J G Baxter, Loughborough (GB); Stephen J Brough, Loughborough (GB); Thomas McInally, Loughborough (GB)

(73) Assignee: AstraZeneca UK Limited, London (GB)

(*) Notice: Subject to any disclaimer, the term of this patent is extended or adjusted under 35 U.S.C. 154(b) by 210 days.

(21) Appl. No.: 09/623,744

(22) PCT Filed: Jul. 18, 2000

(86) PCT No.: PCT/GB00/02756

§ 371 (c)(1),
(2), (4) Date: Sep. 8, 2000

(87) PCT Pub. No.: WO01/05782

PCT Pub. Date: Jan. 25, 2001

(30) Foreign Application Priority Data

Jul. 21, 1999 (SE) .............................. 9902765

(51) Int. Cl.[7] .................. A61K 31/445; C07D 401/06
(52) U.S. Cl. .................. 514/326; 514/218; 514/235.5; 514/255; 514/316; 514/318; 540/525; 544/129; 544/370; 546/187; 546/193; 546/208; 546/209; 546/210; 546/211
(58) Field of Search .............................. 514/218, 235.5, 514/255, 316, 318, 326; 540/525; 544/129, 370; 546/187, 193, 208, 209, 210, 211

(56) References Cited

U.S. PATENT DOCUMENTS

| | | | |
|---|---|---|---|
| 5,021,420 A | 6/1991 | Comte et al. | 514/253 |
| 5,036,075 A | 7/1991 | Comte et al. | 514/293 |
| 5,326,771 A | 7/1994 | Heine et al. | 514/316 |
| 5,352,684 A | 10/1994 | Zimmermann et al. | 514/299 |
| 6,046,331 A | 4/2000 | Wong et al. | 544/370 |
| 6,323,223 B1 | 11/2001 | Gong et al. | 514/331 |
| 6,339,087 B1 | 1/2002 | Gong et al. | 514/252.12 |

FOREIGN PATENT DOCUMENTS

| | | |
|---|---|---|
| DE | 2139084 A | 2/1973 |
| EP | 0350403 A1 | 1/1990 |
| EP | 0546389 A1 | 6/1993 |
| EP | 0 903 349 A2 | 3/1999 |
| WO | WO 91/15484 A1 | 10/1991 |
| WO | WO 99/31060 A2 | 6/1999 |
| WO | WO 00/14066 * | 3/2000 |

OTHER PUBLICATIONS

Cohen et al. "Cytokine function: a study in biologic diversity" CA 125:31427 (1996).*
Jiang et al. "Periodontal pathogens simulate CC–chemokine . . . " CA 132:249805 (1999).*

* cited by examiner

*Primary Examiner*—Ceila Chang
(74) *Attorney, Agent, or Firm*—Morgan, Lewis & Bockius LLP

(57) ABSTRACT

The invention provides compounds of general formula (I)

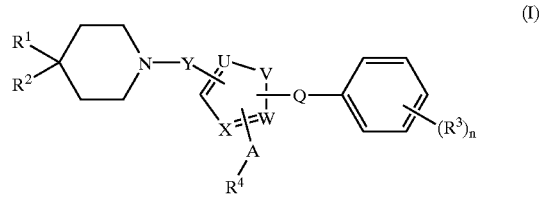

wherein $R^1$, $R^2$, $R^3$, $R^4$, A, Q, U, V, W, X, Y and n are as defined in the specification, processes for their preparation, pharmaceutical compositions containing them and their use in therapy, especially for the treatment of chemokine receptor related diseases and conditions.

12 Claims, No Drawings

DIPHENYL-PIPERIDINE DERIVATIVE

This application is a 371 of PCT/GB00/02756 filed Jul. 8, 2000.

FIELD OF THE INVENTION

The present invention relates to novel compounds, processes for their preparation, pharmaceutical compositions containing them and their use in therapy.

BACKGROUND OF THE INVENTION

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. The chemokine superfamily can be divided into two main groups exhibiting characteristic structural motifs, the Cys-X-Cys (C-X-C) and Cys-Cys (C-C) is families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CXCR1, CXCR2, CXCR3 and CXCR4. These receptors represent good targets for drug development since agents which modulate these receptors would be useful in the treatment of disorders and diseases such as those mentioned above.

DISCLOSURE OF THE INVENTION

In accordance with the present invention, there is provided a compound of formula (I)

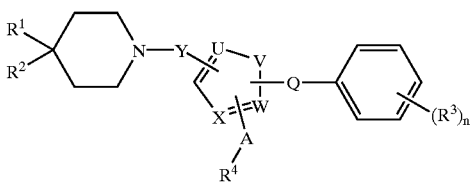

(I)

wherein:
$R^1$ and $R^2$ independently represent phenyl optionally substituted by halogen, C1 to 6 alkyl, nitro, cyano, hydroxy, methylenedioxy, C1 to 6 alkoxy, C1 to 6 haloalkyl, C1 to 6 haloalkoxy or C1 to 6 alkylsulphonyl;
each $R^3$ independently represents halogen, nitro, C1 to 6 alkyl, cyano, C1 to 6 haloalkyl, hydroxy or C1 to 6 alkoxy; each alkoxy group being optionally further substituted by halogen, $NR^5R^6$, $CO_2R^7$, $CONR^8R^9$, pyrazolidinone, or a five membered heteroaromatic ring incorporating one to three heteroatoms independently selected from N, O and S; said heteroaromatic ring being optionally further substsituted by one or more C1 to 4 alkyl groups;
n represents an integer 0 to 3;
$R^4$ represents hydrogen, hydroxy or $NR^{10}R^{11}$;
A represents —CO—, —CH$_2$— or a bond;
Q represents C1 to 4 alkylene;
U, W and X independently represent carbon, optionally substituted by C1 to 4 alkyl, or nitrogen;
V represents nitrogen, optionally substituted by C1 to 4 alkyl, or oxygen;
Y represents C1 to 4 alkylene or —CO—;
$R^5$, $R^6$, $R^7$, $R^8$, $R^9$ independently represent hydrogen or C1 to 6 alkyl;
$R^{10}$ and $R^{11}$ independently represent hydrogen, C2 to 6 unsaturated alkyl or C1 to 6 alkyl; each alkyl group being optionally further substituted by $CO_2R^{12}$, hydroxy, C1 to 6 alkoxy, $CONH_2$, $NR^{13}R^{14}$, $OCH_2CH_2OH$, or a five or six membered saturated or unsaturated heterocyclic ring containing one or two heteroatoms selected from N, O and S; said ring optionally comprising one ring carbon atom that forms a carbonyl group; and said ring being optionally further substituted by C1 to 4 alkyl;
or the group $NR^{10}R^{11}$ together represents a 4 to 8 membered saturated azacyclic ring system; said ring optionally comprising one additional ring heteroatom selected from N, O and S; said ring optionally comprising one ring carbon atom that forms a carbonyl group; and said ring being optionally further substituted by C1 to 6 alkyl, C1 to 6 hydroxyalkyl, hydroxy, $CO_2R^{15}$, $CONH_2$, CHO or $COCH_3$;
$R^{12}$ and $R^{15}$ independently represent hydrogen or C1 to 4 alkyl; and
$R^{13}$ and $R^{14}$ independently represent hydrogen, C1 to 4 alkyl or C1 to 4 alkanoyl;
or a pharmaceutically acceptable salt or solvate thereof.

In one preferred embodiment, V represents nitrogen.
Preferably, $R^3$ represents halogen. More preferably, $R^3$ represents chlorine.

The term "C1 to 6 alkyl" referred to herein denotes a straight or branched chain alkyl group having from 1 to 6 carbon atoms and/or a cyclic alkyl group having from 3 to 6 carbon atoms. Examples of such groups include methyl, ethyl, n-propyl, i-propyl, n-butyl, i-butyl, t-butyl, cyclopentyl, methylcyclopentyl and cyclohexyl.

The term "C1 to 4 alkyl" is to be interpreted analogously.

The term "C2 to 6 unsaturated alkyl" referred to herein denotes a straight or branched chain alkyl group having from 2 to 6 carbon atoms and including one double bond or one triple is bond or a cyclic alkyl group having from 3 to 6 carbon atoms and including one double bond. Examples of such groups include ethenyl, ethynyl, 1- and 2-propenyl, 1- and 2-propynyl, 2-methyl-2-propenyl, 2-butenyl, 2-butynyl, cyclopentenyl and cyclohexenyl.

The term "C1 to 6 alkoxy" referred to herein denotes an oxygen atom bonded to a straight or branched chain alkyl group having from 1 to 6 carbon atoms or an oxygen atom bonded to a cyclic alkyl group having from 3 to 6 carbon atoms. Examples of such groups include methoxy, ethoxy, n-propoxy, i-propoxy, n-butoxy, i-butoxy, s-butoxy, t-butoxy, cyclopropyloxy and cyclohexyloxy.

The term "halogen" referred to herein denotes fluorine, chlorine, bromine and iodine.

The terms "C1 to 6 haloalkyl" (for example, chloromethyl, 2-fluoroethyl and trifluoromethyl), "C1 to 6 haloalkoxy" (for example, trifluoromethoxy) and "C1 to 6 hydroxyalkyl" (for example, hydroxymethyl, 1-hydroxyethyl or 2-hydroxyethyl) are to be interpreted analogously.

Similarly, the term "C1 to 6 alkylsulphonyl" represents such groups as methylsulphonyl, t-butylsulphonyl and cyclohexylsulphonyl.

The term "C1 to 4 alkanoyl" referred to herein denotes a carbonyl group bonded to a straight or branched chain alkyl group having from 1 to 3 carbon atoms. Examples of such groups include acetyl and propionyl.

Examples of a "five membered heteroaromatic ring incorporating one to three heteroatoms independently selected from N, O and S" include furan, thiophene, imidazole, isoxazole, thiazole and triazole.

Examples of a "five or six membered saturated or unsaturated heterocyclic ring containing one or two heteroatoms selected from N, O and S; said ring optionally comprising one ring carbon atom that forms a carbonyl group" include morpholine, pyrrolidine, pyridine, tetrahydrofuran, imidazole, pyrrolidone, piperidone and piperazine.

Examples of a "4 to 8 membered saturated azacyclic ring system optionally incorporating one further heteroatom independently selected from N, O and S" include pyrrolidine, piperidine, morpholine, piperazine, pyrazolidine, imidazolidine, and perhydroazepine.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Examples of particular compounds of the invention include:

1-[(1-benzyl-1H-pyrazol-3-yl)methyl]-4,4-diphenylpiperidine;

1-{[1-(3-chlorobenzyl)-1H-pyrazol-3-yl]methyl}-4,4-diphenylpiperidine;

1-{[1-(3,4-dimethylbenzyl)-1H-pyrazol-3-yl]methyl}-4,4-diphenylpiperidine;

1-{[1-(4-methylbenzyl)-1H-pyrazol-3-yl]methyl}-4,4-diphenylpiperidine;

4,4-diphenyl-1-({1-[4-(trifluoromethyl)benzyl]-1H-pyrazol-3-yl}methyl)piperidine;

1-{[1-(2,4-dichlorobenzyl)-1H-pyrazol-3-yl]methyl}-4,4-diphenylpiperidine;

1-{[1-(3,4-dichlorobenzyl)-1H-pyrazol-3-yl]methyl}-4,4-diphenylpiperidine;

1-{[1-(3,4-difluorobenzyl)-1H-pyrazol-3-yl]methyl]-4,4-diphenylpiperidine;

1-{[1-(4-chlorobenzyl)-1H-pyrazol-3-yl]methyl}-4,4-diphenylpiperidine;

1-{[1-(4-fluorobenzyl)-1H-pyrazol-3-yl]methyl}-4,4-diphenylpiperidine;

1-{[1-(4-chloro-2-methoxybenzyl)-1H-pyrazol-3-yl]methyl}-4,4-diphenylpiperidine;

5-chloro-2-({3-[(4,4-diphenyl-1-piperidinyl)methyl]-1H-pyrazol-1-yl}methyl)phenol;

2-[5-chloro-2-({3-[(4,4-diphenyl-1-piperidinyl)methyl]-1H-pyrazol-1-yl}methyl)phenoxy]-N,N-dimethylacetamide;

1-{[1-(4-chlorobenzyl)-1H-imidazol-4-yl]methyl}-4,4-diphenylpiperidine;

1-(4-chlorobenzyl)-3-[(4,4-diphenyl-1-piperidinyl)methyl]-1H-pyrazole-4-carbaldehyde;

{1-(4-chlorobenzyl)-3-[(4,4-diphenyl-1-piperidinyl)methyl]-1H-pyrazol-4-yl}methanol;

1-{[1-(4-chlorobenzyl)-1H-1,2,3-triazol-5-yl]methyl}-4,4-diphenylpiperidine;

1-{[1-(4-chlorobenzyl)-1H-1,2,3-triazol-4-yl]methyl}-4,4-diphenylpiperidine;

1-(4-chlorobenzyl)-4-[(4,4-diphenyl-1-piperidinyl)methyl]-1H-imidazole-5-carboxylic acid;

1-(4-chlorobenzyl)-4-[(4,4-diphenyl-1-piperidinyl)methyl]-1H-imidazole-5-carboxamide;

1-{[2-(4-chlorobenzyl)-1H-imidazol-5-yl]methyl}-4,4-diphenylpiperidine;

1-{[2-(4-chlorobenzyl)-1-methyl-1H-imidazol-5-yl]methyl}-4,4-diphenylpiperidine;

1-{[2-(4-chlorobenzyl)-3-methyl-3H-imidazol-5-yl]methyl}-4,4-diphenylpiperidine;

[2-(4-chlorobenzyl)-1H-imidazol-5-yl](4,4-diphenyl-1-piperidinyl)methanone;

2-[4-({1-(4-chlorobenzyl)-3-[(4,4-diphenyl-1-piperidinyl)methyl]-1H-pyrazol-4-yl}methyl)-1-piperazinyl]-1-ethanol;

4-({1-(4-chlorobenzyl)-3-[(4,4-diphenyl-1-piperidinyl)methyl]-1H-pyrazol-4-yl}methyl)-1-piperazinecarbaldehyde;

1-[4-({1-(4-chlorobenzyl)-3-[(4,4-diphenyl-1-piperidinyl)methyl]-1H-pyrazol-4-yl}methyl)-1-piperazinyl]-1-ethanone;

$N^1$-({1-(4-chlorobenzyl)-3-[(4,4-diphenyl-1-piperidinyl)methyl]-1H-pyrazol-4-yl}methyl)-$N^1,N^2,N^2$-trimethyl-1,2-ethanediamine;

N-({1-(4-chlorobenzyl)-3-[(4,4-diphenyl-1-piperidinyl)methyl]-1H-pyrazol-4-yl}methyl)-2-(4-morpholinyl)-1-ethanamine;

1-{[4-(1-azetidinylmethyl)-1-(4-chlorobenzyl)-1H-pyrazol-3-yl]methyl}-4,4-diphenylpiperidine;

N-({1-(4-chlorobenzyl)-3-[(4,4-diphenyl-1-piperidinyl)methyl]-1H-pyrazol-4-yl}methyl)-2-(1-pyrrolidinyl)-1-ethanamine;

N-({1-(4-chlorobenzyl)-3-[(4,4-diphenyl-1-piperidinyl)methyl]-1H-pyrazol-4-yl}methyl)-beta-alanine;

2-[({1-(4-chlorobenzyl)-3-[(4,4-diphenyl-1-piperidinyl)methyl]-1H-pyrazol-4-yl)methyl]amino]acetic acid;

N-({1-(4-chlorobenzyl)-3-[(4,4-diphenyl-1-piperidinyl)methyl]-1H-pyrazol-4-yl}methyl)-2-(2-pyridinyl)-1-ethanamine;

{1-(4-chlorobenzyl)-3-[(4,4-diphenyl-1-piperidinyl)methyl]-1H-pyrazol-4-yl}-N-(4-pyridinylmethyl)methanamine;

2-[1-({1-(4-chlorobenzyl)-3-[(4,4-diphenyl-1-piperidinyl)methyl]-1H-pyrazol-4-yl}methyl)-4-piperidinyl]-1-ethanol;

1-({1-(4-chlorobenzyl)-3-[(4,4-diphenyl-1-piperidinyl)methyl]-1H-pyrazol-4-yl}methyl)-4-methyl-1,4-diazepane;

3-[5-chloro-2-({3-[(4,4-diphenyl-1-piperidinyl)methyl]-1H-pyrazol-1-yl}metayl)phenoxy]-N,N-dimethyl-1-propanamine;

2-[5-chloro-2-({3-[(4,4-diphenyl-1-piperidinyl)methyl]-1H-pyrazol-1-yl}methyl)phenoxy]acetic acid;

2-[5-chloro-2-({3-[(4,4-diphenyl-1-piperidinyl)methyl]-1H-pyrazol-1-yl}methyl)phenoxy]acetamide;

2-[5-chloro-2-({3-[(4,4-diphenyl-1-piperidinyl)methyl]-1H-pyrazol-1-yl}methyl)phenoxy]-N,N-dimethylacetamide;

2-[5-chloro-2-({3-[(4,4-diphenyl-1-piperidinyl)methyl]-1H-pyrazol-1-yl}methyl)phenoxy]-N,N-diethylacetamide;

2-[5-chloro-2-({3-[(4,4-diphenyl-1-piperidinyl)methyl]-1H-pyrazol-1-yl}methyl)phenoxy]propanamide;

2-[5-chloro-2-({3-[(4,4-diphenyl-1-piperidinyl)methyl]-1H-pyrazol-1-yl}methyl)phenoxy]-N-methylacetamide;

1-{2-[5-chloro-2-({3-[(4,4-diphenyl-1-piperidinyl)methyl]-1H-pyrazol-1-yl}methyl)phenoxy]acetyl}-3-pyrazolidinone;

1-[(1-{4-chloro-2-[(3,5-dimethyl-4-isoxazolyl)methoxy]benzyl}-1H-pyrazol-3-yl)methyl]-4,4-diphenylpiperidine;

5-chloro-2-({3-[(4,4-diphenyl-1-piperidinyl)methyl]-1H-pyrazol-1-yl}methyl)phenyl (1-methyl-1H-imidazol-2-yl)methyl ether;

5-chloro-2-({3-[(4,4-diphenyl-1-piperidinyl)methyl]-1H-pyrazol-1-yl}methyl)phenyl (2-methyl-1,3-thiazol-4-yl)methyl ether;

{1-(4-chlorobenzyl)-4-[(4,4-diphenyl-1-piperidinyl)methyl]-1H-imidazol-5-yl}(4-morpholinyl)methanone;

1-(4-chlorobenzyl)-4-[(4,4-diphenyl-1-piperidinyl)methyl]-N,N-dimethyl-1H-imidazole-5-carboxamide;

1-(4-chlorobenzyl)-4-[(4,4-diphenyl-1-piperidinyl)methyl]-N-(2-methoxyethyl)-1H-imidazole-5-carboxamide;

1-(4-chlorobenzyl)-4-[(4,4-diphenyl-1-piperidinyl)methyl]-N-(4-hydroxycyclohexyl)-1H-imidazole-5-carboxamide;

1-(4-chlorobenzyl)-4-[(4,4-diphenyl-1-piperidinyl)methyl]-N-[1-(hydroxymethyl)propyl]-1H-imidazole-5-carboxamide;

1-(4-chlorobenzyl)-4-[(4,4-diphenyl-1-piperidinyl)methyl]-N-(tetrahydro-2-furanylmethyl)-1H-imidazole-5-carboxamide;

{1-(4-chlorobenzyl)-4-[(4,4-diphenyl-1-piperidinyl)methyl]-1H-imidazol-5-yl}[2-(hydroxymethyl)-1-piperidinyl]methanone;

1-(4-chlorobenzyl)-N-[3-(diethylamino)propyl]-4-[(4,4-diphenyl-1-piperidinyl)methyl]-1H-imidazole-5-carboxamide;

{1-(4-chlorobenzyl)-4-[(4,4-diphenyl-1-piperidinyl)methyl]-1H-imidazol-5-yl}[3-(hydroxymethyl)-1-piperidinyl]methanone;

1-(4-chlorobenzyl)-4-[(4,4-diphenyl-1-piperidinyl)methyl]-N-(2-hydroxyethyl)-1H-imidazole-5-carboxamide;

1-(4-chlorobenzyl)-4-[(4,4-diphenyl-1-piperidinyl)methyl]-N-(2-hydroxyethyl)-N-methyl-1H-imidazole-5-carboxamide;

1-(4-chlorobenzyl)-4-[(4,4-diphenyl-1-piperidinyl)methyl]-N-[3-(1H-imidazol-1-yl)propyl]-1H-imidazole-5-carboxamide;

{1-(4-chlorobenzyl)-4-[(4,4-diphenyl-1-piperidinyl)methyl]-1H-imidazol-5-yl}(1-pyrrolidinyl)methanone;

{1-(4-chlorobenzyl)-4-[(4,4-diphenyl-1-piperidinyl)methyl]-1H-imidazol-5-yl}(3-hydroxy-1-pyrrolidinyl)methanone;

1-[4-({1-(4-chlorobenzyl)-4-[(4,4-diphenyl-1-piperidinyl)methyl]-1H-imidazol-5-yl}carbonyl)-1-piperazinyl]-1-ethanone;

{1-(4-chlorobenzyl)-4-[(4,4-diphenyl-1-piperidinyl)methyl]-1H-imidazol-5-yl}(1-piperidinyl)methanone;

1-(4-chlorobenzyl)-N-[2-(diethylamino)ethyl-4-[(4,4-diphenyl-1-piperidinyl)methyl-N-(2-hydroxyethyl)-1H-imidazole-5-carboxamide;

1-(4-chlorobenzyl)-4-[(4,4-diphenyl-1-piperidinyl)methyl]-N-[2-(4-morpholinyl)ethyl]-1H-imidazole-5-carboxamide;

1-(4-chlorobenzyl)-4-[(4,4-diphenyl-1-piperidinyl)methyl]-N-ethyl-N-(2-hydroxyethyl)-1H-imidazole-5-carboxamide;

{1-(4-chlorobenzyl)-4-[(4,4-diphenyl-1-piperidinyl)methyl]-1H-imidazol-5-yl}(4-ethyl-1-piperazinyl)methanone;

N-(2-amino-2-oxoethyl)-1-(4-chlorobenzyl)-4-[(4,4-diphenyl-1-piperidinyl)methyl]-1H-imidazole-5-carboxamide;

1-(4-chlorobenzyl)-4-[(4,4-diphenyl-1-piperidinyl)methyl]-N-[2-(1-pyrrolidinyl)ethyl]-1H-imidazole-5-carboxamide;

1-(4-chlorobenzyl)-4-[(4,4-diphenyl-1-piperidinyl)methyl]-N-[2-(1H-imidazol-4-yl)ethyl]-1H-imidazole-5-carboxamide;

1-(4-chlorobenzyl)-4-[(4,4-diphenyl-1-piperidinyl)methyl]-N-methyl-1H-imidazole-5-carboxamide;

1-(4-chlorobenzyl)-N-(2,3-dihydroxypropyl)-4-[(4,4-diphenyl-1-piperidinyl)methyl]-1H-imidazole-5-carboxamide;

1-(4-chlorobenzyl)-4-[(4,4-diphenyl-1-piperidinyl)methyl]-N-[(1-ethyl-2-pyrrolidinyl)methyl]-1H-imidazole-5-carboxamide;

ethyl 1-({1-(4-chlorobenzyl)-4-[(4,4-diphenyl-1-piperidinyl)methyl]-1H-imidazol-5-yl}carbonyl)-4-piperidinecarboxylate;

ethyl 1-({1-(4-chlorobenzyl)-4-[(4,4-diphenyl-1-piperidinyl)methyl]-1H-imidazol-5-yl]carbonyl)-3-piperidinecarboxylate; methyl 3-[({1-(4-chlorobenzyl)-4-[(4,4-diphenyl-1-piperidinyl)methyl]-1H-imidazol-5-yl}carbonyl)amino]propanoate;

methyl 2-[({1-(4-chlorobenzyl)-4-[(4,4-diphenyl-1-piperidinyl)methyl]-1H-imidazol-5-yl}carbonyl)amino]acetate;

1-(4-chlorobenzyl)-4-[(4,4-diphenyl-1-piperidinyl)methyl]-N-(2-pyridinylmethyl)-1H-2-imidazole-5-carboxamide;

1-(4-chlorobenzyl)-4-[(4,4-diphenyl-1-piperidinyl)methyl]-N-[2-(2-pyridinyl)ethyl]-1H-imidazole-5-carboxamide;

1-(4-chlorobenzyl)-4-[(4,4-diphenyl-1-piperidinyl)methyl]-N-(3-pyridinylmethyl)-1H-imidazole-5-carboxamide;

1-(4-chlorobenzyl)-4-[(4,4-diphenyl-1-piperidinyl)methyl]-N-(2-hydroxy-1,1-dimethylethyl)-1H-imidazole-5-carboxamide;

1-(4-chlorobenzyl)-4-[(4,4-diphenyl-1-piperidinyl)methyl]-N-(2-hydroxy-1-methylethyl)-1H-imidazole-5-carboxamide;

1-(4-chlorobenzyl)-4-[(4,4-diphenyl-1-piperidinyl)
  methyl]-N-[3-(2-oxo-1-pyrrolidinyl)propyl]-1H-
  imidazole-5-carboxamide;
N-[2-(acetylamino)ethyl]-1-(4-chlorobenzyl)-4-[(4,4-
  diphenyl-1-piperidinyl)methyl]-1H-imidazole-5-
  carboxamide;
1-(4-chlorobenzyl)-4-[(4,4-diphenyl-1-piperidinyl)
  methyl]-N-[2-(2-hydroxyethoxy)ethyl]-1H-imidazole-
  5-carboxamide;
1-(4-chlorobenzyl)-4-[(4,4-diphenyl-1-piperidinyl)
  methyl]-N-[1-(hydroxymethyl)cyclopentyl]-1H-
  imidazole-5-carboxamide;
1-(4-chlorobenzyl)-4-[(4,4-diphenyl-1-piperidinyl)
  methyl]-N-[2-hydroxy-1-(hydroxymethyl)ethyl]-1H-
  imidazole-5-carboxamide;
1-(4-chlorobenzyl)-4-[(4,4-diphenyl-1-piperidinyl)
  methyl]-N-(3-methoxypropyl)-1H-imidazole-5-
  carboxamide;
1-({1-(4-chlorobenzyl)-4-[(4,4-diphenyl-1-piperidinyl)
  methyl]-1H-imidazol-5-yl}carbonyl)-2-
  pyrrolidinecarboxamide;
1-({1-(4-chlorobenzyl)-4-[(4,4-diphenyl-1-piperidinyl)
  methyl]-1H-imidazol-5-yl}carbonyl)-2-
  pyrrolidinecarboxamide;
{1-(4-chlorobenzyl)-4-[(4,4-diphenyl-1-piperidinyl)
  methyl]-1H-imidazol-5-yl}[4-(2-hydroxyethyl)-1-
  piperidinyl]methanone;
1-(4-chlorobenzyl)-4-[(4,4-diphenyl-1-piperidinyl)
  methyl]-N-(2-propynyl)-1H-imidazole-5-
  carboxamide;
4-({1-(4-chlorobenzyl)-4-[(4,4-diphenyl-1-piperidinyl)
  methyl]-1H-imidazol-5-yl}carbonyl)-2-piperazinone;
1-(4-chlorobenzyl)-4-[(4,4-diphenyl-1-piperidinyl)
  methyl]-N-[1-(hydroxymethyl)propyl]-1H-imidazole-
  5-carboxamide;
1-{3-(4-chlorobenzyl)-[1,2,4]oxadiazol-5-ylmethyl}4,4-
  diphenylpiperidine;
and pharmaceutically acceptable salts and solvates thereof.

The present invention further provides a process for the preparation of a compound of formula (I) which comprises:

(i) when Y represents CH$_2$,
reductive amination of a compound of general formula (II)

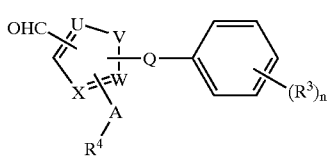

(II)

wherein R$^3$, R$^4$, A, Q, U, V, W, X and n are as defined in formula (I),
with a compound of formula (III)

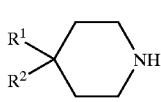

(III)

wherein R$^1$ and R$^2$ are as defined in formula (I); or
(ii) when Y represents C1 to 4 alkyl,
reacting a compound of general formula (IV)

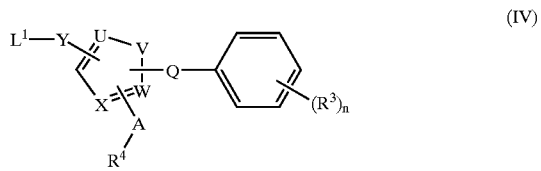

(IV)

wherein R$^3$, R$^4$, A, Q, U, V, W, X and n are as defined in formula (I) and L$^1$ is a leaving group,
with a compound of formula (III); or
(iii) when Y represents CO, reacting a compound of general formula (V)

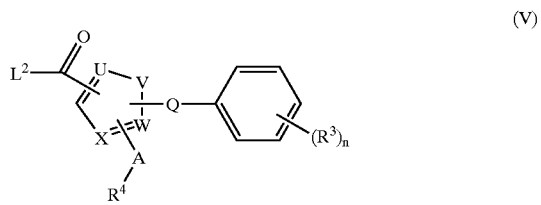

(V)

wherein R$^3$, R$^4$, A, Q. U, V, W, X and n are as defined in formula (I) and L is a leaving group,
with a compound of formula (III); or
(iv) when at least one R group in formula (I) represents optionally substituted
reacting a compound of formula (VI)

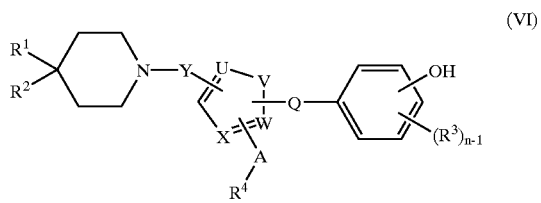

(VI)

wherein R$^1$, R$^2$, R$^3$, R$^4$, A, Q, U, V, W, X, Y and n are as defined in formula (I), with a compound of formula (VII)

R—L$^3$ (VII)

wherein R$^3$ is such that the resultant group OR represents an optionally substituted C1 to 6 alkoxy group as defined for R$^3$ in formula (I), and L is a leaving group;

(v) when A represents CO and R$^4$ represents NR$^{10}$OR$^{11}$, reacting a compound of formula (VIII)

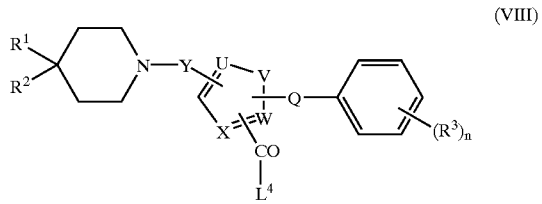

(VIII)

wherein R$^1$, R$^2$, R$^3$, Q, U, V, W, X, Y and n are as defined in formula (I), and L$^4$ is a leaving group, with a compound of formula (IX)

HNR$^{10}$R$^{11}$ (IX)

wherein $R^{10}$ and $R^{11}$ are as defined in formula (I); or (vi) when A represents $CH_2$ and $R^4$ represents $NR^{10}R^{11}$, reductive amination of a compound of formula (X)

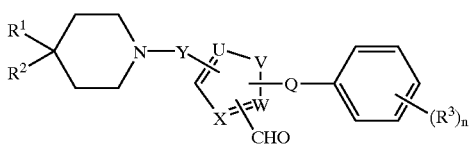
(X)

wherein $R^1$, $R^2$, $R^3$, Q, U, V, W, X, Y and n are as defined in formula (I), with a compound of formula (IX)

(IX)

wherein $R^{10}$ and $R^{11}$ are as defined in formula (I); or (vii) when Q is bonded to V and V represents nitrogen, reacting a compound of formula (XI)

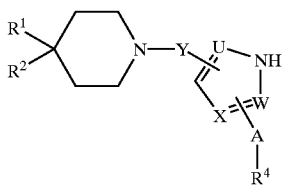
(XI)

wherein $R^1$, $R^2$, $R^4$, A, U, W, X and Y are as defined in formula (I), with a compound of formula (XII)

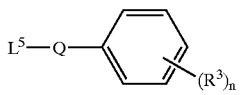
(XII)

wherein $R^3$, Q and n are as defined in formula (I) and $L^5$ is a leaving group;
and optionally after (i), (ii), (iii), (iv), (v), (vi) or (vii) converting the compound of formula (I) to a further compound of formula (I) and/or forming a pharmaceutically acceptable salt or solvate of the compound of formula (I).

Salts of compounds of formula (I) may be formed by reacting the free base or another salt thereof, with one or more equivalents of the appropriate acid. The reaction may be carried out in a solvent in which the salt is insoluble, or in a solvent in which the salt is soluble, followed by subsequent removal of the solvent in vacuo or by freeze drying. Suitable solvents include, for example, water, dioxan, ethanol, 2-propanol, tetrahydrofuran or diethyl ether, or mixtures thereof. The reaction may also be carried out on an ion exchange resin.

In processes (i) and (vi), the reductive amination reaction generally takes place under conditions which will be known to persons skilled in the art. For example, treatment of an aldehyde with an amine in the presence of a reducing agent in an inert solvent. Suitable reducing systems include catalytic hydrogenation or borane and derivatives thereof. A partial list of such reagents can be found in "Advanced Organic Chemistry", J. March (1985) 3$^{rd}$ Edition on page 799.

In processes (ii) and (vii), the reaction is performed by treating an amine of general formula (III) or (XI) with an electrophile of general formula (IV) or (XII) respectively in an inert solvent. Suitable leaving groups L and L include sulfonate, trifluorosulfonate, mesylate, tosylate, and halides selected from the group chloride, bromide or iodide. The reaction is generally performed in the presence of a base. This base can be either an excess of the amine nucleophile or can be an additive to the reaction mixture. Potential basic additives are metal carbonates, especially alkali metal carbonates such as cesium carbonate, metal oxides and hydroxides, and tertiary amine bases. Suitable organic solvents are those such as acetonitrile, dioxane, N,N-dimethylformamide, N-methyl-2-pyrrolidinone, tetrahydrofuran, dimethylsulfoxide, sulfolane and C1 to 4 alcohols. In a preferred embodiment, the leaving group is chloride.

In processes (iii) and (v) above, the reaction will take place on stirring a mixture of the reactants in a suitable organic solvent at a suitable temperature, generally between 0° C. and the boiling point of the solvent. The reaction time will depend inter alia on the solvent used, the reaction temperature and the nature of the leaving group. The reaction may be catalysed by the addition of a base; bases that may be used include organic amines (for example, triethylamine or pyridine) and alkali metal hydroxides, alkoxides, carbonates or hydrides.

Suitable leaving groups, $L^2$ and $L^4$, include halogen (especially chlorine) and hydroxyl. When the leaving group is OH, the reaction between compounds of formulae (V) and (In), or between compounds of formulae (VIII) and (IX) may also be achieved using a suitable coupling agent such as CDI (1,1'-carbonyldiimidazole), DCC (1,3-dicyclohexylcarbodiimide) or HOBt (1-hydroxybenzotriazole).

In process (iv), the reaction will generally take place under similar conditions to those described above for processes (ii) and (vii).

In general, compounds of formulae (H), (IV), (V), (VI), (VII) (X) and (XI) may be prepared using similar types of reactions to those described above for compounds of formula (I).

Compounds of formula (H) wherein Q is bonded to V and V represents nitrogen, may be prepared by reaction of a compound of formula (XIII)

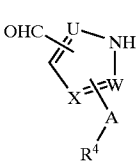
(XIII)

wherein A, U, W, X and $R^4$ are as defined in formula (I), with a compound of formula (XII) using conditions similar to those described above for processes (ii) and (vii).

Compounds of formulae (IV), (V) or (VIII) wherein $L^1$, $L^2$ and $L^4$ respectively are leaving groups may be prepared from the corresponding compounds wherein $L^1$, $L^2$ and $L^4$ are OH using reactions that will be readily apparent to the man skilled in the art. Thus, for example, using thionyl chloride or methanesulphonyl chloride in the presence of a suitable base such as triethylamine.

Compounds of formulae (IV) or (V) wherein $L^1$ and $L^2$ are OH and wherein Q is bonded to V and V represents nitrogen, may be prepared by a process analogous to that described above for compounds of formula (II).

Compounds of formula (VI) may be prepared by demethylation of a corresponding compound of formula (XIV)

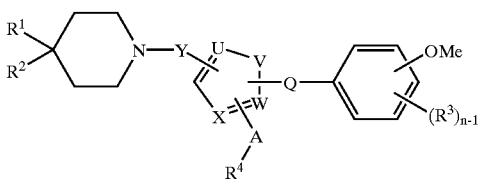

(XIV)

wherein $R^1$, $R^2$, $R^3$, $R^4$, A, Q, U, V, W, X, Y and n areas defined in formula (I), using, for example, boron tribromide.

Compounds of formula (X) may be prepared by formylation of a corresponding compound of formula (XV)

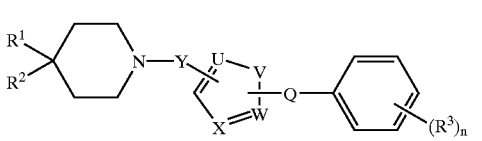

(XV)

wherein $R^1$, $R^2$, $R^3$, Q, U, V, W, X, Y and n are as defined in formula (I), using for example phosphorus oxychloride in N,N-dimethylformamide.

Compounds of formula (II) may be similarly prepared by formylation of a corresponding compound of formula (XVI)

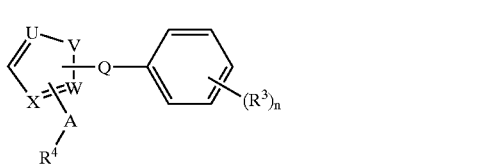

(XVI)

Certain novel intermediates of formulae (II), (IV), (V), (VI), (VII), (X), (XI), (XV) and (XVI) form another aspect of the invention.

Compounds of formulae (III), (VII), (IX), (XII) and (XII) are either commercially available, or are known in the literature or may be prepared using known techniques.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the addition and subsequent removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

Certain compounds of formula (I) are capable of existing in stereoisomeric forms. It will be understood that the invention encompasses the use of all geometric and optical isomers of the compounds of formula (I) and mixtures thereof including racemates. The use of tautomers and mixtures thereof also form an aspect of the present invention.

The compounds of the invention and intermediates may be isolated from their reaction mixtures, and if necessary further purified, by using standard techniques.

The compounds of formula (I) have activity as pharmaceuticals, in particular as modulators of chemokine receptor activity. More particularly, the compounds have utility as modulators of the activity of chemokine receptors CCR1 and/or CCR3.

A further aspect of the invention involves the use of a compound of general formula (I) in the treatment of conditions or diseases in which modulation of chemokine receptor activity is beneficial.

Thus, compounds of general formula (I) may be used in the treatment of autoimmune, inflammatory, proliferative and hyperproliferative diseases and immunologically-mediated diseases including rejection of transplanted organs or tissues and Acquired Immunodeficiency Syndrome (AIDS).

Examples of these conditions include:

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, osteoarthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, inflammatory bowel disease, irritable bowel syndrome, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura; and (6) (allograft rejection) acute and chronic following, for example, transplantation of kidney, heart, liver, lung, bone marrow, skin and cornea; and chronic graft versus host disease.

Thus, the present invention provides a compound of formula (I), or a pharmaceutically-acceptable salt or solvate thereof, as hereinbefore defined for use in therapy.

In a further aspect, the present invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention also provides a method of treating an inflammatory disease in a person suffering from, or at risk of, said disease, which comprises administering to the person a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The invention will now be further explained by reference to the following illustrative examples.

EXAMPLE 1

1-[(1-Benzyl-1H-pyrazol-3-yl)methyl]-4,4-diphenylpiperidine

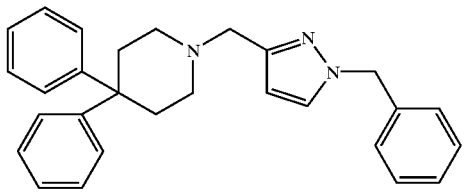

(a) 1-Benzyl-1H-pyrazole-3-carbaldehyde

To a solution of benzyl bromide (0.29 g) in N,N-dimethylformamide (9 ml) was added 1H-pyrazole-3-carboxaldehyde (0.15 g) and potassium carbonate (0.24 g). The mixture was stirred at room temperature for 24 hours, silica gel was added, the solvent removed by evaporation and the crude material purified by chromatography (isohexane:ether, 2:1) to give the product as an oil (0.18 g).

$^1$H NMR δ (CDCl$_3$) 10.0 (s, 1H), 7.5–7.2 (mn, 5H), 6.8 (d, 1H), 5.4 (s, 2H).

(b) 1-[(1-Benzyl-1H-pyrazol-3-yl)methyl]-4,4-diphenylpiperidine

The product from step (a) (0.17 g) was dissolved in ethanol (3 ml) and a solution of 4,4-diphenylpiperidine (0.118 g) in ethanol (1 ml) added. A solution of sodium cyanoborohydride (1.0 M in tetrahydrofuran, 3.0 ml) was added and the solution stirred at room temperature for 16 hours. Silica gel was added, the solvent removed by evaporation and the crude material purified by chromatography (dichloromethane:methanol, 100:0 to 95:5) to give the product as an oil. Further purification by supercritical fluid chromatography gave the product as a solid (0.010 g), m.p. 167–168° C.

MS: APCI(+ve) 400 (M+H); $^1$H NMR δ (CDCl$_3$) 7.4–7.0 (m, 16H), 6.64 (d, 1H), 5.25 (s, 2H), 4.0 (s, 2H 8H).

EXAMPLE 2

1-{[1-(3-Chlorobenzyl)-1H-pyrazol-3-yl]methyl}-4,4-diphenylpiperidine

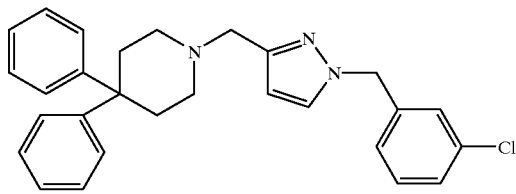

Prepared by the method of Example 1 using 3-chlorobenzyl bromide in step (a) to give the product as a solid (0.011 g), m.p. 136–137° C.

MS: APCI(+ve) 442/44 (M+H); $^1$H NMR δ (CDCl$_3$) 7.42 (d, 1H), 7.4–7.0 (m, 14H), 6.6 (d, 1H), 5.2 (s, 2H), 4.0 (s, 3.4–2.6 (m, 8H).

EXAMPLE 3

1-{[1-(3,4-Dimethylbenzyl)-1H-pyrazol-3-yl]methyl}-4,4-diphenylpiperidine

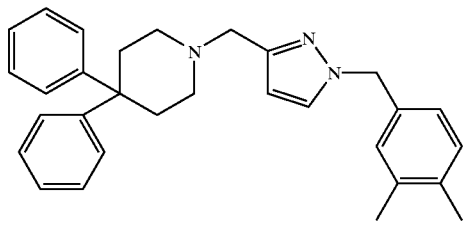

Prepared by the method of Example 1 using 3,4-dimethylbenzyl chloride in step (a) to give the product as a solid (0.015 g), m.p. 139–140° C.

MS: APCI(+ve) 436 (M+H); $^1$H NMR δ (CDCl$_3$) 7.45–6.8 (m, 14H), 6.6 (d, 1H), 5.16 (s, 2H), 4.0 (s, 2H), 3.4–2.6 (m, 8H), 2.2 (m, 6H).

EXAMPLE 4

1-{[1-(4-Methylbenzyl)-1H-pyrazol-3-yl]methyl}-4,4-diphenylpiperidine Dihydrochloride

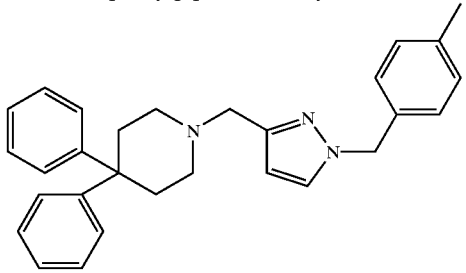

Prepared by the method of Example 1 using 4-methylbenzyl bromide in step (a) to give the product as an oil. Treatment with 1.0M ethereal hydrogen chloride solution gave the product as a solid (0.010 g), m.p. 147–148° C.

MS: APCI(+ve) 422 (M+H); $^1$H NMR δ (CDCl$_3$) 7.4–6.8 (m, 16H), 5.2 (s, 2H), 4.1 (s, 2H), 3.6–2.6 (m, 8H), 2.0 (s, 3H).

EXAMPLE 5

4,4-Diphenyl-1-({1-[4-(trifluoromethyl)benzyl]-1H-pyrazol-3-yl}methyl)piperidine Dihydrochloride

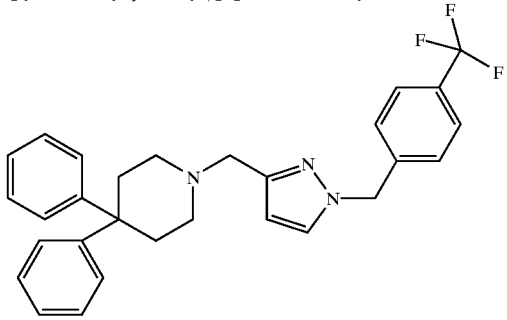

Prepared by the method of Example 1 using 4-trifluoromethylbenzyl chloride in step (a) to give the product as an oil. Treatment with 1.0M ethereal hydrogen chloride solution gave the product as a solid (0.022 g), m.p. 66–67° C.

MS: APCI(+ve) 476/78 (M+H); $^1$H NMR δ (CDCl$_3$) 7.6 (d, 2H), 7.5–7.1 (m, 13H), 6.9 (bs, 1H), 5.3 (s, 2H), 4.1 (s, 2H), 3.6–2.6 (m, 8H).

EXAMPLE 6

1-{[1-(2,4-Dichlorobenzyl)-1H-pyrazol-3-yl]methyl}-4,4-diphenylpiperidine Dihydrochloride

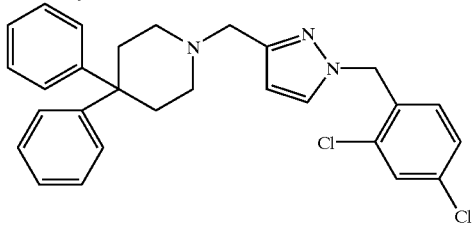

Prepared by the method of Example 1 using 2,4-dichlorobenzyl chloride in step (a) to give the product as an oil. Treatment with 1.0M ethereal hydrogen chloride solution gave the product as a solid (0.022 g), m.p. 101–102° C.

MS: APCI(+ve) 476/78 (M+H); $^1$H NMR δ (CDCl$_3$) 7.6–6.8 (m, 15H), 5.3 (bs, 2H), 4.1 (bs, 2H), 3.6–2.4 (m, 8H).

EXAMPLE 7

1-{[1-(3,4-Dichlorobenzyl)-1H-pyrazol-3-yl]methyl}-4,4-diphenylpiperidine Dihydrochloride

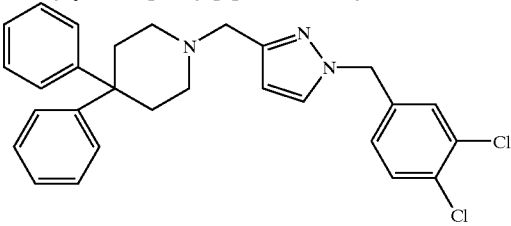

Prepared by the method of Example 1 using 3,4-dichlorobenzyl chloride in step (a) to give the product as an oil. Treatment with 1.0M ethereal hydrogen chloride solution gave the product as a solid (0.022 g), m.p. 191–192° C.

MS: APCI(+ve) 476/78 (M+H); $^1$H NMR δ (CDCl$_3$) 7.5–6.9 (m, 15H), 5.2 (s, 2H), 4.1 (s, 2H), 3.6–2.6 (m, 8H).

EXAMPLE 8

1-{[1-(3,4-Difluorobenzyl)-1H-pyrazol-3-yl]methyl}-4,4-diphenylpiperidine

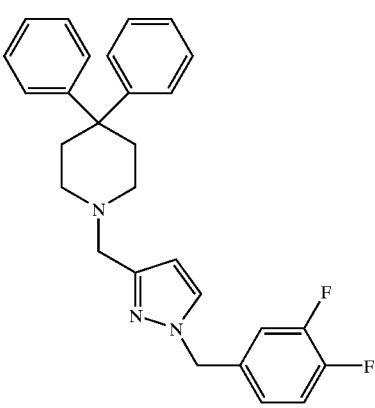

(a) 1-(3,4-Difluorobenzyl)-1H-pyrazole-3-carbaldehyde

Prepared by the method of Example 1 step (a) using 3,4-difluorobenzyl bromide to give the product as an oil (1.2 g).

$^1$H NMR δ (CDCl$_3$) 10.0 (s, 1H), 7.46 (d, 1H), 7.3–6.9 (m, 3H), 6.82 (d, 1H), 5.35 (s, 2H).

(b) 1-{[1-(3,4-Difluorobenzyl)-1H-pyrazol-3-yl]methyl}-4,4-diphenylpiperidine Hydrochloride The product of step (a) (0.23 g) was dissolved in ether (10 ml), 4,4-diphenylpiperidine (0.25 g) was added and the solution cooled to 0° C. Titanium tetraisopropoxide (0.34 ml) was added, the solution stirred for 1 hour and titanium tetrachloride (0.13 ml) added. After a further 30 minutes at 0° C. a solution of BH$_3$.SMe$_2$ (2.0M in tetrahydrofuran, 0.5 ml) was added and the mixture allowed to warm to room temperature over 20 hours. 2.0M Aqueous sodium hydroxide solution was added, followed by ethyl acetate. The mixture was stirred for 1 hour and the insoluble solids removed by filtration through Kieselgur gel. The aqueous phase of the filtrate was separated, ethyl acetate was added, the organic phases combined, washed with brine, dried and the solvent removed to give a gum. Purification by chromatography (dichloromethane:methanol, 10:1) gave an oil. Treatment with 1.0M ethereal hydrogen chloride solution gave the product as a solid (0.20 g), m.p. 236–237° C.

MS: APCI(+ve) 476/78 (M+H); $^1$H NMR δ (d$_6$-DMSO) 10.6 (bs, 1H), 7.91 (d, 1H), 7.5–7.0 (m, 13H), 6.5 (d, 1H), 5.3 (s, 2H), 4.2 (d, 2H), 3.5–2.3 (m, 8H).

EXAMPLE 9

1-{[1-(4-Chlorobenzyl)-1H-pyrazol-3-yl]methyl}-4,4-diphenylpiperidine Dihydrochloride

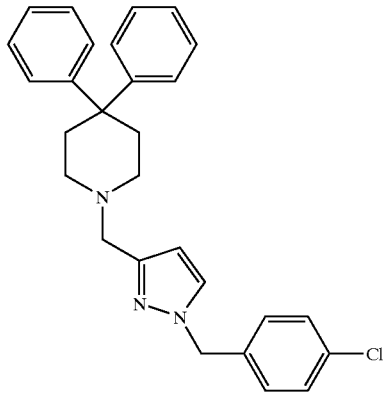

Prepared by the method of Example 8 using 4-chlorobenzyl chloride in step (a) to give the product as an oil. Treatment with 1.0M ethereal hydrogen chloride solution gave the product as a solid (0.09 g), m.p. 137–138° C.

MS: APCI(+ve) 442/44 (M+H); $^1$H NMR δ (d$_6$-DMSO) 7.88 (d, 1H), 7.5–7.1 (m, 14H), 6.5 (d, 1H), 5.3 (s, 2H), 3.5–2.5 (m, 8H).

EXAMPLE 10

1-{[1-(4-Fluorobenzyl)-1H-pyrazol-3-yl]methyl}-4,4-diphenylpiperidine Hydrochloride

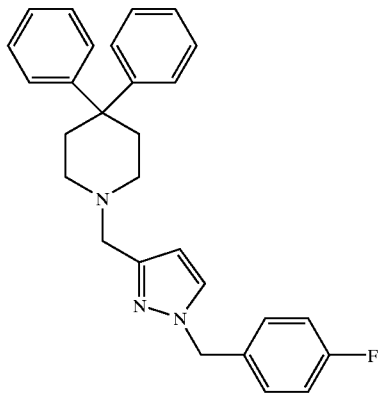

Prepared by the method of Example 8 using 4-fluorobenzyl chloride in step (a) to give the product as an oil. Treatment with 1.0M ethereal hydrogen chloride solution gave the product as a solid (0.085 g), m.p. 192–193° C.

MS: APCI(+ve) 426 (M+H); $^1$H NMR δ (d$_6$-DMSO) 11.0 (bs, 1H), 7.85 (d, 1H), 7.5–7.1 (m, 14H), 6.5 (d, 1H), 5.3 (s, 2H), 4.2 (d, 2H), 3.5–2.4 (m, 8H).

EXAMPLE 11

1-{[1-(4-Chloro-2-methoxybenzyl)-1H-pyrazol-3-yl]methyl}-4,4-diphenylpiperidine Hydrochloride

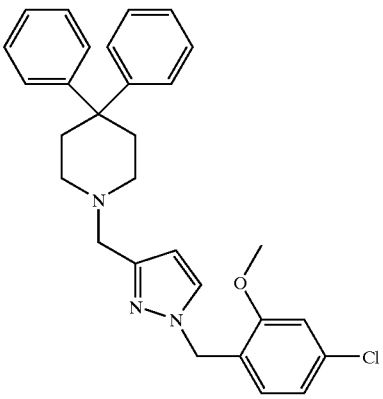

Prepared by the method of Example 8 using 4-chloro-2-methoxybenzyl chloride in step (a) to give the product as an oil. Treatment with 1.0M ethereal hydrogen chloride solution gave the product as a solid (0.025 g), m.p. 73–74° C.

MS: ESI(+ve) 472.21 (M+H); $^1$H NMR δ (d$_6$-DMSO) 12.6 (bs, 1H), 7.4–6.8 (m, 15H), 5.2 (s, 2H), 4.0 (s, 2H), 3.8 (s, 3H), 3.6–2.4 (m, 8H).

EXAMPLE 12

5-Chloro-2-({3-[(4,4-diphenyl-1-piperidinyl)methyl]-1H-pyrazol-1-yl}methyl)phenol Dihydrochloride

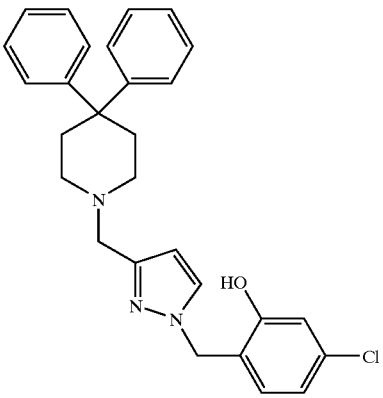

The product of Example 11 (0.4 g) was dissolved in dichloromethane (8.5 ml), cooled to 0° C. and a solution of boron tribromide (1.0M in dichloromethane, 8.5 ml) added. After 24 hours the solvent was removed by evaporation to leave a residue which was dissolved in methanol, the solvent was removed and the residue dissolved in 2.0M aqueous hydrogen chloride solution. After 24 hours the product was obtained as a solid (0.39 g), m.p. 260–261° C.

MS: ESI(+ve) 458.19 (M+H); $^1$H NMR δ (d$_6$-DMSO) 10.4 (bs, 2H), 7.8 (d, 1H), 7.5–6.8 (m, 13H), 6.42 (d, 1H), 5.2 (s, 2H), 4.2 (d, 2H), 3.5–2.2 (m, 8H).

EXAMPLE 13

2-[5-Chloro-2-({3-[(4,4-diphenyl-1-piperidinyl)methyl]-1H-pyrazol-1-yl}methyl)phenoxy]-N,N-dimethylacetamide Hydrochloride

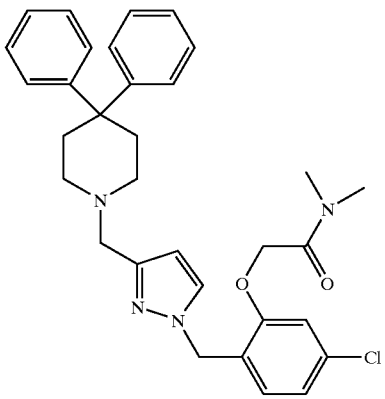

The product of Example 12 (0.1 g) was dissolved in N,N-dimethylformamide (5 ml) in a 10 ml Wheaton vial, cesium carbonate (0.2 g) and 2-chloro-N,N-dimethylacetamide (0.05 g) were added and the mixture heated at 70° C. for 2 hours. The mixture was cooled, water and ethyl acetate were added and the organic phase separated, dried and concentrated to a residue. Purification by chromatography (dichloromethane:methanol:0.880 ammonia solution, 90:10:1) gave a gum. Treatment with 1.0M ethereal hydrogen chloride solution gave the product as a solid (0.016 g), m.p. 181–182° C.

MS: ESI(+ve) 543.25 (M+H); $^1$H NMR δ (CDCl$_3$) 7.7–6.8 (m, 15H), 5.26 (s, 2H), 4.7 (s, 2H), 4.0 (s, 2H), 3.6–2.4 (m, 14H).

EXAMPLE 14

1-{[1-(4-Chlorobenzyl)-1H-imidazol-4-yl]methyl}-4,4-diphenylpiperidine Dihydrochloride

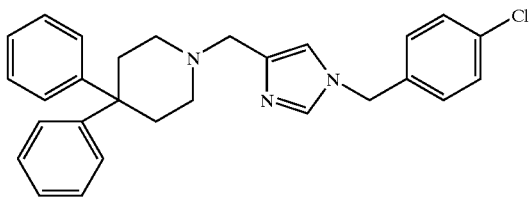

(a) [1-(4-Chlorobenzyl)-1H-imidazol-4-yl]methanol

4-Chlorobenzylchloride (1.2 g) was dissolved in N,N-dimethylformamide (20 ml), 4(5)-hydroxymethylimidazole hydrochloride (1.0 g) and potassium carbonate (4 g) were added and the mixture heated at 90° C. for 20 hours. Water and ethyl acetate were added, the organic phase was separated, washed with brine, dried and the solvent removed by evaporation. The residue was purified by chromatography (dichloromethane:methanol, 9:1) to give the product as a mixture of regioisomers (0.5 g). This material was used in the next step without further purification.

(b) 1-{[1-(4-Chlorobenzyl)-1H-imidazol-4-yl]methyl}-4,4-diphenylpiperidine

The product of step (a) (0.39 g) was dissolved in toluene (10 ml), triethylamine (0.26 ml) and thionyl chloride (0.13 ml) were added and the mixture stirred at room temperature for 20 hours. The solvent was removed by evaporation, a solution of 4,4-diphenylpiperidine hydrochloride (0.478 g) in dimethylsulphoxide (10 ml) and triethylamine (0.65 ml) added. After 2 hours water and ethyl acetate were added, the organic phase was separated, washed with brine, dried and the solvent removed to leave a gum. Purification by super-critical fluid chromatography gave a solid which was treated with 1.0M ethereal hydrogen chloride solution to give the product as a solid (0.02 g), m.p. 254–255° C.

MS: APCI(+ve) 442/44 (M+H); $^1$H NMR δ (d$_6$-DMSO) 9.2 (bs, 1H), 8.05 (s, 1H), 7.7–7.0 (m, 15H), 5.4 (s, 2H), 4.4 (s, 2H), 3.6–2.6 (m, 8H).

EXAMPLE 15

1-(4-Chlorobenzyl)-3-[(4,4-diphenyl-1-piperidinyl)methyl]-1H-pyrazole-4-carbaldehyde

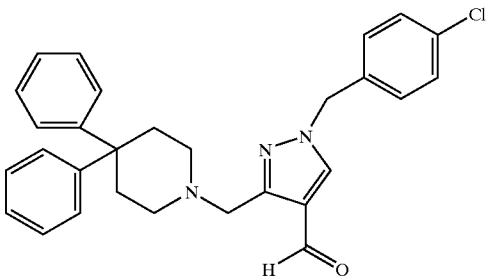

The product of Example 9 (0.11 g) was dissolved in N,N-dimethylformamide (1 ml), phosphorus oxychloride (0.023 ml) was added, the solution was heated at 70° C. for 16 hours, then at 100° C. for 20 hours. The solution was cooled, ice, water and ethyl acetate were added and the organic phase separated and dried. The solvent was removed by evaporation to give a residue which was purified by chromatography (dichloromethane: methanol, 8:2) to give the product as a solid (0.03 g), m.p. 133–134° C.

MS: APCI(+ve) 470 (M+H); $^1$H NMR δ (CDCl$_3$) 10.0 (s, 1H), 7.8 (s, 1H), 7.4–7.0 (m, 14H), 5.2 (s, 2H), 3.7 (s, 2H), 2.7–2.4 (m, 8H).

EXAMPLE 16

{1-(4-Chlorobenzyl)-3-[(4,4-diphenyl-1-piperidinyl)methyl]-1H-pyrazol-4-yl}methanol

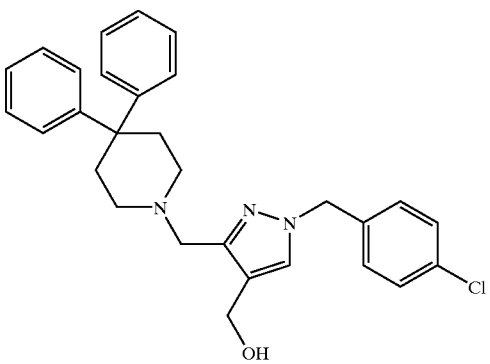

The product of Example 15 (0.05 g) was dissolved in dichloromethane (5 ml) and sodium triacetoxyborohydride (0.068 g) added. After 20 hours at room temperature, brine and dichloromethane were added, the organic phase was separated, dried and the solvent removed by evaporation to give a residue. Trituration under ether gave the product as a solid (0.028 g), m.p. 104–105° C.

MS: ESI(+ve) 472.21 (M+H); $^1$H NMR δ (CDCl$_3$) 7.5–7.0 (m, 15H), 5.34 (bs, 1H), 5.18 (s, 2H), 4.7 (s, 2H), 4.1 (s, 2H), 3.8–2.6 (m, 8H).

EXAMPLE 17

1-{[1-(4-Chlorobenzyl)-1H-1,2,3-triazol-5-yl]methyl}-4,4-diphenylpiperidine

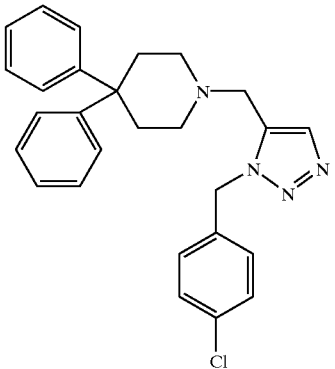

(a) [1-(4-Chlorobenzyl)-1H-1,2,3-triazol-5-yl]methanol and [1-(4-Chlorobenzyl)-1H-1,2,3-triazol-4-yl]methanol 1-Azidomethyl-4-chlorobenzene (5.6 g) was dissolved in dioxane (100 ml), propargyl alcohol (1.67 g) was added and the solution heated under reflux for 72 hours. The solution was cooled, water and ethyl acetate were added, the organic phase separated, and concentrated to an oil. Purification by chromatography (dichloromethane:ethyl acetate, 1:1 to 0:1) gave the products as oils:

First eluted isomer: [1-(4-chlorobenzyl)-1H-1,2,3-triazol-5-yl]methanol (1.66 g); $^1$H NMR δ (d$_6$-DMSO) 7.68 (s, 1H), 7.4–7.2 (dd, 4H), 5.59 (s, 2H), 5.52 (s, 1H), 4.53 (d, 2H).

Second eluted isomer: [1-(4-chlorobenzyl)-1H-1,2,3-triazol-4-yl]methanol (1.76 g); $^1$H NMR δ (d$_6$-DMSO) 8.0 (s, 1H), 7.46–7.34 (dd, 4H), 5.57 (s, 2H), 5.15 (t, 1H), 4.51 (d, 2H).

(b) 1-{[1-(4-Chlorobenzyl)-1H-1,2,3-triazol-5-yl]methyl}-4,4-diphenylpiperidine

The first eluted isomer from step (a) (0.1 g) was dissolved in dichloromethane (2 ml), methanesulphonyl chloride (0.035 ml) and triethylamine (0.062 ml) were added and the mixture stirred at room temperature for 16 hours. A solution of 4,4-diphenylpiperidine hydrochloride (0.122 g) in N,N-dimethylformamide (1 ml) and triethylamine (0.062 ml) were added and the mixture stirred for 48 hours. Ethyl acetate and brine were added, the organic phase separated and concentrated to a gum which was purified by chromatography (dichloromethane:ethyl acetate, 4:1) to give the product a solid which was recrystallised from acetonitrile to give the product as a solid (0.060 g), m.p. 195° C.

MS: APCI(+ve) 443/5 (M+H); $^1$H NMR δ (CDCl$_3$) 7.6 (s, 1H), 7.35–7.1(m, 14H), 5.65 (s, 2H), 3.2 (s, 2H), 2.36 (bs, 8H).

EXAMPLE 18

1-{[1-(4-Chlorobenzyl)-1H-1,2,3-triazol-4-yl]methyl}-4,4-diphenylpiperidine

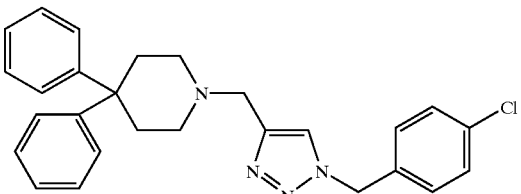

Prepared by the method of Example 17 (b) using the product of Example 17 step (a) second eluted isomer to give a solid. Purification by HPLC gave the product as a solid (0.036 g), m.p. 148° C.

MS: ESI(+ve) 443.19 (M+H); $^1$H NMR δ (CDCl$_3$) 7.4–7.1 (m, 15H), 5.46 (s, 2H), 3.59 (s, 2H), 2.6 (m, 4H), 2.42 (m, 4H).

EXAMPLE 19

1-(4-Chlorobenzyl)-4-[(4,4-diphenyl-1-piperidinyl)methyl]-1H-imidazole-5-carboxylic Acid

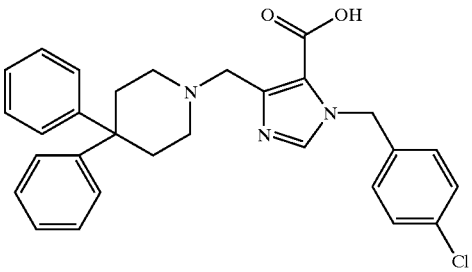

(a) Methyl 1-(4-Chlorobenzyl)-4-(hydroxymethyl)-1H-imidazole-5-carboxylate

Prepared by the method of Example 14 step (a) using methyl 4-hydroxymethyl-1H-imidazolecarboxylate (3.69 g) to give the product as a mixture of regioisomers (1.8 g). The mixture was used directly in the next step without further purification.

(b) Methyl 1-(4-Chlorobenzyl)-4-[(4,4-diphenyl-1-piperidinyl)methyl]-1H-imidazole-5-carboxylate Prepared by the method of Example 14 step (b) to give an oil which was purified by chromatography (ethyl acetate:triethylamine, 95:5) to give the product as a solid (0.9 g).

$^1$H NMR δ (CDCl$_3$) 7.6 (s, 1H), 7.35–7.0 (m, 14H), 5.4 (s, 2H), 3.94 (s, 3H), 3.7 (s, 2H), 2.62 (bm, 4H), 2.45 (m, 4H).

(c) 1-(4-Chlorobenzyl)-4-[(4,4-diphenyl-1-piperidinyl)methyl]-1H-imidazole-5-carboxylic Acid The product of step (b) (0.5 g) was dissolved in methanol (20 ml) and 2N aqueous sodium hydroxide solution (10 ml) added. After 16 hours 2M aqueous hydrochloric acid was added and the pH adjusted to pH 6 by the addition of aqueous sodium bicarbonate solution. Ethyl acetate was added, the organic phase was separated, dried and the solvent removed by evaporation to give the product as a solid (0.35 g), m.p. 135–136° C.

MS: APCI(+ve) 486/88 (M+H); $^1$H NMR δ (CDCl$_3$) 7.5–7.0 (m, 15H), 5.65 (s, 2H), 3.9 (s, 2H), 3.3 (d, 2H), 2.8 (m, 4H), 2.5 (m, 2H).

EXAMPLE 20

1-(4-Chlorobenzyl)-4-[(4,4-diphenyl-1-piperidinyl)methyl]-1H-imidazole-5-carboxamide

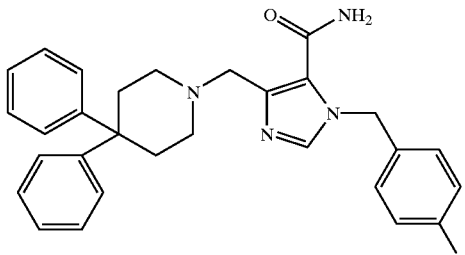

The product of Example 19 (0.03 g) was dissolved in N,N-dimethylformamide (2 ml), N,N-carbonyldiimidazole (0.020 g) was added and the solution heated at 60° C. for 2 hours and cooled. Aqueous ammonia solution (1 ml) was added and the mixture stirred at room temperature for 16 hours. Brine and ethyl acetate were added, the organic phase was separated, dried and the solvent removed by evaporation to give a solid. Trituration under ether gave the product as a solid (0.014 g), m.p. 227–228° C.

MS: APCI(+ve) 485/87 (M+H); $^1$H NMR δ (d$_6$-DMSO) 10.4 (bs, 1H), 7.4 (s, 1H), 7.39–7.1 (m, 14H), 5.5 (s, 2H), 5.4 (bs, 2H), 3.6 (s, 2H), 2.7–2.2 (bm, 8H).

EXAMPLE 21

1-{[2-(4-Chlorobenzyl)-1H-imidazol-5-yl]methyl}-4,4-diphenylpiperidine Dihydrochloride

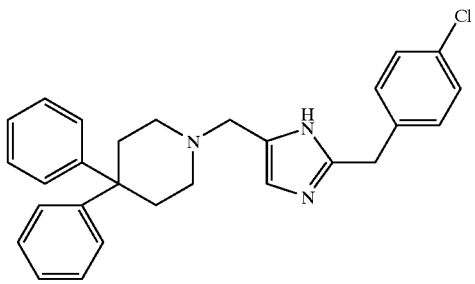

Prepared by the method of Example 14 using 2-(4-chlorobenzyl)-4-(hydroxymethyl)imidazole (1.0 g), and 4,4-diphenylpiperidine (1.23 g) to give a residue which was purified by chromatography (ethyl acetate:methanol, 95:5) to give a solid. This material was further purified by chromatography (dichloromethane:methanol aqueous ammonia solution, 97:3:0.1) to give a solid, which on treatment with 1.0M ethereal hydrogen chloride solution gave the product as a solid (0.07 g), m.p. 186–187° C.

MS: ESI(+ve) 442.2 (M+H); $^1$H NMR δ (CDCl$_3$) 7.6–7.0 (m, 15H), 4.4 (bs, 2H), 3.6–1.6 (bm, 10H).

EXAMPLE 22

1-{[2-(4-Chlorobenzyl)-1-methyl-1H-imidazol-5-yl]methyl}-4,4-diphenylpiperidine Dihydrochloride and 1-{[2-(4-Chlorobenzyl)-3-methyl-3H-imidazol-5-yl]methyl}-4,4-diphenylpiperidine Dihydrochloride

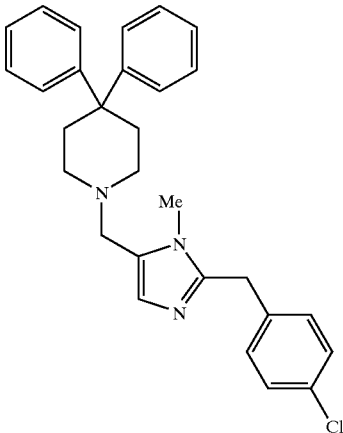

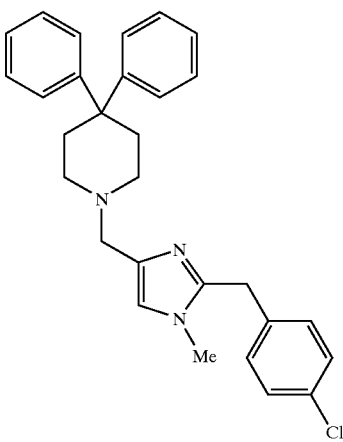

(a) [2-(4-Chlorobenzyl)-1-methyl-1H-imidazol-5-yl]methanol and [2-(4-Chlorobenzyl)-1-methyl-1H-imidazol-4-yl]methanol 2-(4-Chlorobenzyl)-4-(hydroxymethyl)imidazole (1.0 g) was dissolved in N,N-dimethylformamide (20 ml), and sodium hydride (60% dispersion in oil, 0.18 g) added. After 1 hour at room temperature methyl iodide (0.28 ml) was added and the solution stirred at room temperature for 2 hours. Water and ethyl acetate were added, the organic phase separated and the solvent removed to give a gum. Purification by chromatography (dichloromethane:methanol, 97:3) gave the product as a mixture of regioisomers as a solid (0.5 g). This mixture was used directly in the next step without further purification.

(b) 1-{[2-(4-Chlorobenzyl)-1-methyl-1H-imidazol-5-yl]methyl}-4,4-diphenylpiperidine and 1-{[2-(4-Chlorobenzyl)-3-methyl-3H-imidazol-5-yl]methyl}-4,4-diphenylpiperidine Prepared by the method of Example 14 step (b) to give the product as a mixture of regioisomers. Purification by supercritical fluid chromatography gave the separated products as oils.

Treatment of the first eluted oil with 1.0M ethereal hydrogen chloride solution gave the product as a solid (0.01 g), m.p. 252–253° C.

MS: APCI(+ve) 456 (M+H); $^1$H NMR δ (CDCl$_3$) 7.3–7.0 (m, 14H), 6.75 (s, 1H), 4.0 (s, 2H), 3.4 (s, 3H), 3.3 (s, 2H), 2.4 (m, 8H).

Treatment of the second eluted oil with 1.0M ethereal hydrogen chloride solution gave the product as a solid (0.01 g), m.p. 248–249° C.

MS: APCI(+ve) 456 (M+H); $^1$H NMR δ (CDCl$_3$) 7.3–7.0 (m, 14H), 6.70 (s, 1H), 4.05 (s, 2H), 3.38 (s, 2H), 3.35 (s, 3H), 2.7–2.4 (m, 8H).

EXAMPLE 23

[2-(4-Chlorobenzyl)-1H-imidazol-5-yl](4,4-diphenyl-1-piperidinyl)methanone

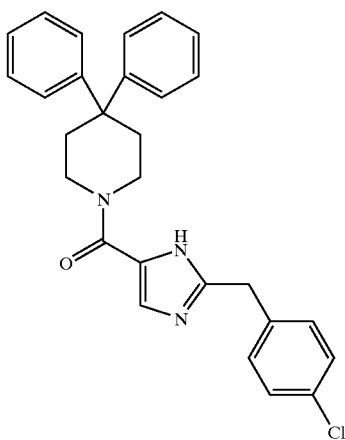

(a) Ethyl 2-(4-Chlorobenzyl)-1H-imidazole-5-carboxylate

4-Chloro-N-hydroxy-benzeneethanimidamide (1.0 g) and ethyl propiolate (0.53 g) were dissolved in methanol (20 ml), heated under reflux for 20 hours and cooled to room temperature. The residue was dissolved in diphenylether, heated under reflux for 1 hour, cooled to room temperature and iso-hexane (300 ml) added. A solid was produced which was collected by filtration, triturated under ether and dried to give the product as a solid (0.1 g).

$^1$H NMR δ (CDCl$_3$) 7.6 (s, 1H), 7.3 (d, 2H), 7.15 (d, 2H), 4.3 (q, 2H), 4.05 (s, 2H), 1.4 (t, 3H).

(b) [2-(4-Chlorobenzyl)-1H-imidazol-5-yl](4,4-diphenyl-1-piperidinyl)methanone

The product from step (a) (0.07 g) was dissolved in methanol (5 ml), 2N aqueous sodium hydroxide solution was added and the solution stirred at room temperature for 20 hours. The solvent was removed by evaporation, 2N aqueous hydrochloric acid was added and the solvent removed. The residue was dissolved in thionyl chloride (10 ml), the solution heated under reflux for 2 hours, cooled and evaporated. The residue was dissolved in dichloromethane (5 ml), 4,4-diphenylpiperidine (0.073 g) and triethylamine (1 ml) added and the solution stirred at room temperature for 2 hours. Brine was added, the organic phase separated and the solvent removed to give a residue which was purified by supercritical fluid chromatography to give the product as a solid (0.03 g), m.p. 105–106° C.

MS: ESI 456.18 (M+H); $^1$H NMR δ (CDCl$_3$) 7.4 7.0 (m, 15H), 4.05 (s, 2H), 3.9 (bm, 3H), 2.95 (bt, 1H), 2.45 (m, 4H), 1.6 (m, 4H).

EXAMPLE 24

2-[4-({1-(4-Chlorobenzyl)-3-[(4,4-diphenyl-1-piperidinyl)methyl]-1H-pyrazol-4-yl}methyl)-1-piperazinyl]-1-ethanol

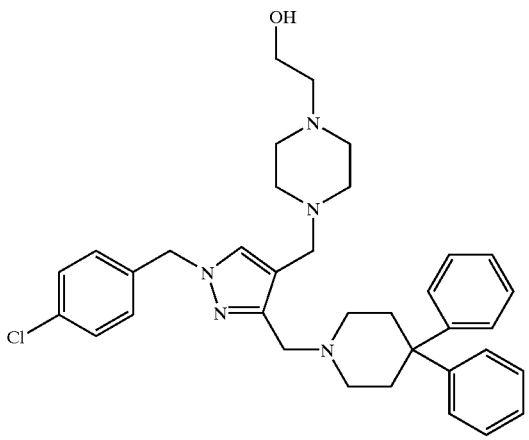

The product of Example 15 (0.001 g) was dissolved in N,N-dimethylformamide (0.2 ml), N-(2-hydroxyethyl)piperazine (0.0008 g) and 1 drop of acetic acid were added. After 1 hour a solution of sodium triacetoxyborohydride (0.0013 g) in N,N-dimethylformamide (0.1 ml) was added and the solution shaken at room temperature for 24 hours. The solvent was removed to give the product as an oil.

MS: APCI(+ve) base peak 583.

Following the general method of Example 24 and using the appropriate amine, the compounds of Examples 25 to 36 were prepared.

EXAMPLE 25

4-({1-(4-Chlorobenzyl)-3-[(4,4-diphenyl-1-piperidinyl)methyl]-1H-pyrazol-4-yl}methyl)-1-piperazinecarbaldehyde

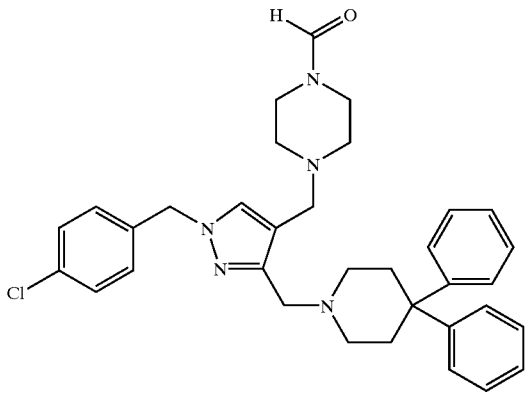

MS: APCI(+ve) base peak 568.

EXAMPLE 26

1-[4-({1-(4-Chlorobenzyl)-3-[(4,4-diphenyl-l1-piperidinyl)methyl]-1H-pyrazol-4-yl}methyl)-1-piperazinyl]-1-ethanone

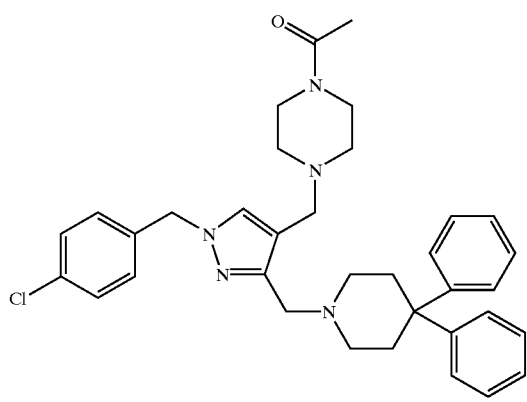

MS: APCI(+ve) base peak 582.

EXAMPLE 27

$N^1$-({1-(4-Chlorobenzyl)-3-[(4,4-diphenyl-1-piperidinyl)methyl]-1H-pyrazol-4-yl}methyl)-$N^1$,$N^2$,$N^2$-trimethyl-1,2-ethanediamine

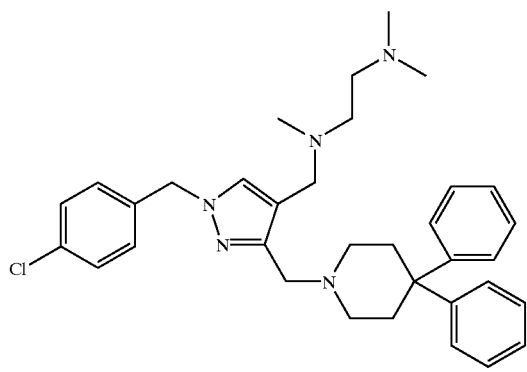

MS: APCI(+ve) base peak 556.

EXAMPLE 28

N-({1-(4-Chlorobenzyl)-3-[(4,4-diphenyl-1-piperidinyl)methyl]-1H-pyrazol-4-yl}methyl)-2-(4-morpholinyl)-1-ethanamine

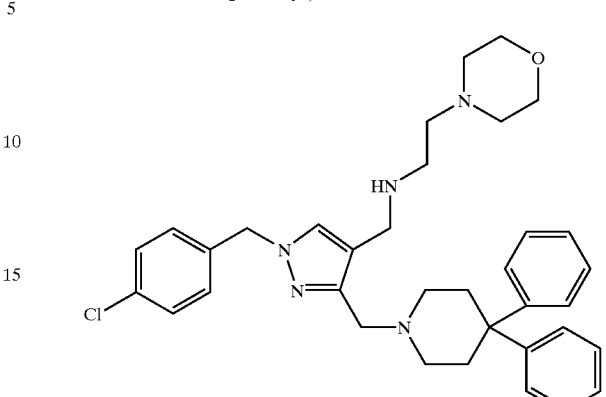

MS: APCI(+ve) base peak 584.

EXAMPLE 29

1-{[4-(1-Azetidinylmethyl)-1-(4-chlorobenzyl)-1H-pyrazol-3-yl]methyl}-4,4-diphenylpiperidine

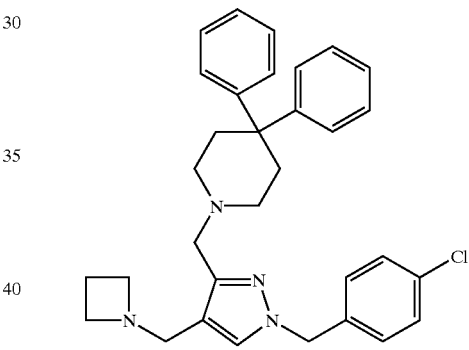

MS: APCI(+ve) base peak 511.

EXAMPLE 30

N-({1-(4-Chlorobenzyl)-3-[(4,4-diphenyl-1-piperidinyl)methyl]-1H-pyrazol-4-yl}methyl)-2-(1-pyrrolidinyl)-1-ethanamine

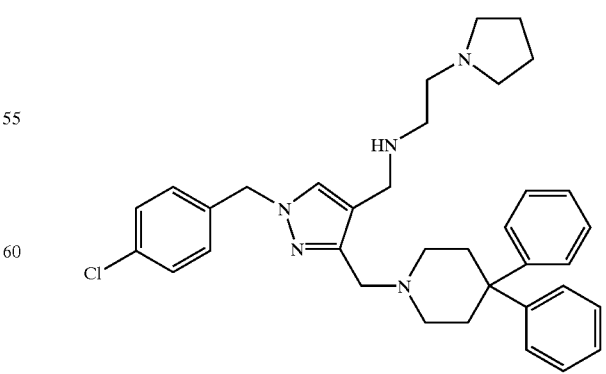

MS: APCI(+ve) base peak 568.

EXAMPLE 31

N-({1-(4-Chlorobenzyl)-3-[(4,4-diphenyl-1-piperidinyl)methyl]-1H-pyrazol-4-yl}methyl)-beta-alanine

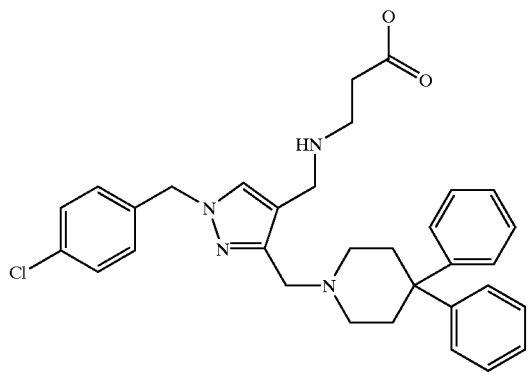

MS: APCI(+ve) base peak 543.

EXAMPLE 32

2-[({1-(4-Chlorobenzyl)-3-[(4,4-diphenyl-1-piperidinyl)methyl]-1H-pyrazol-4-yl}methyl)amino]acetic Acid

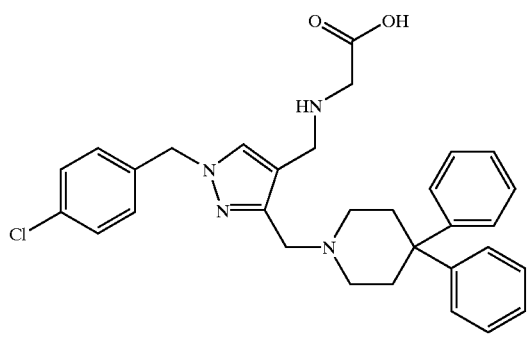

MS: APCI(+ve) base peak 529.

EXAMPLE 33

N-({1-(4-Chlorobenzyl)-3-[(4,4-diphenyl-1-piperidinyl)methyl]-1H-pyrazol-4-yl}methyl)-2-(2-pyridinyl)-1-ethanamine

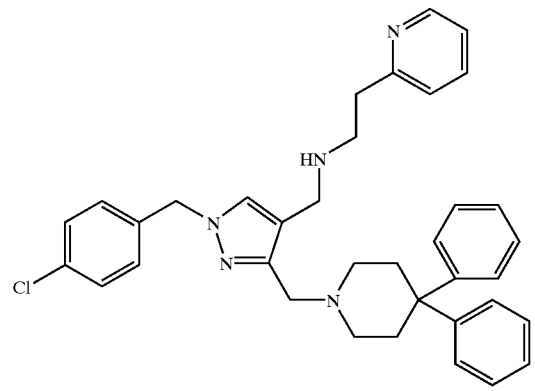

MS: APCI(+ve) base peak 576.

EXAMPLE 34

{1-(4-Chlorobenzyl)-3-[(4,4-diphenyl-1-piperidinyl)methyl]-1H-pyrazol-4-yl}-N-(4-pyridinylmethyl)methanamine

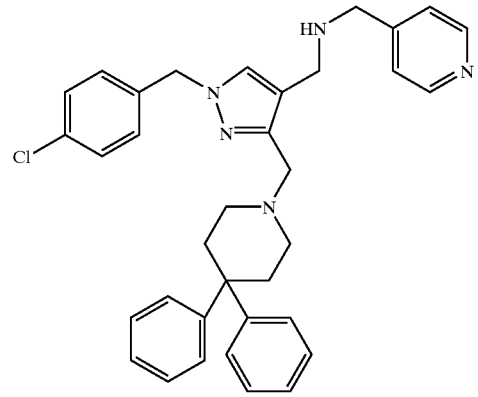

MS: APCI(+ve) base peak 562.

EXAMPLE 35

2-[1-({1-(4-Chlorobenzyl)-3-[(4,4-diphenyl-1-piperidinyl)methyl]-1H-pyrazol-4-yl}methyl)-4-piperidinyl]-1-ethanol

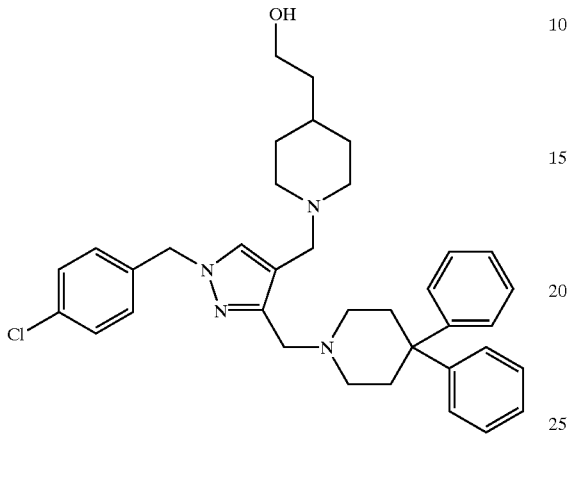

MS: APCI(+ve) base peak 583.

EXAMPLE 36

1-({1-(4-Chlorobenzyl)-3-[(4,4-diphenyl-1-piperidinyl)methyl]-1H-pyrazol-4-yl}methyl)-4-methyl-1,4-diazepane

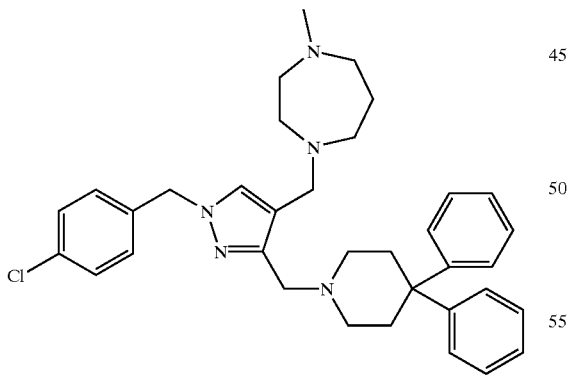

MS: APCI(+ve) base peak 568.

Following the general method of Example 13, the compounds of Examples 37 to 47 were prepared.

EXAMPLE 37

3-[5-Chloro-2-({3-[(4,4-diphenyl-1-piperidinyl)methyl]-1H-pyrazol-1-yl}methyl)phenoxy]-N,N-dimethyl-1-propanamine

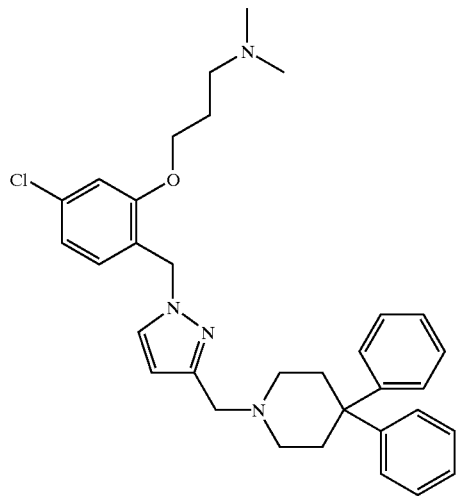

MS: APCI(+ve) base peak 543.

EXAMPLE 38

2-[5-Chloro-2-({3-l(4,4-diphenyl-1-piperidinyl)methyl]-1H-pyrazol-1-yl}methyl)phenoxy]acetic Acid

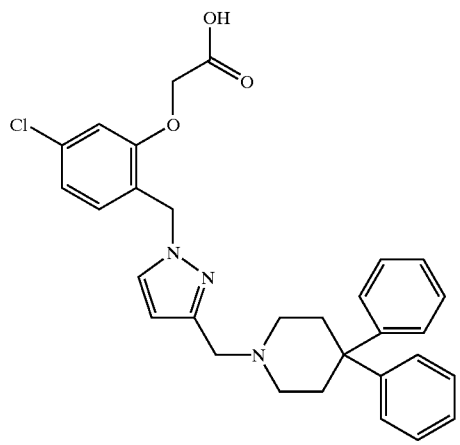

MS: APCI(+ve) base peak 516.

EXAMPLE 39

2-[5-Chloro-2-({3-[(4,4-diphenyl-1-piperidinyl)methyl]-1H-pyrazol-1-yl}methyl)phenoxy]acetamide

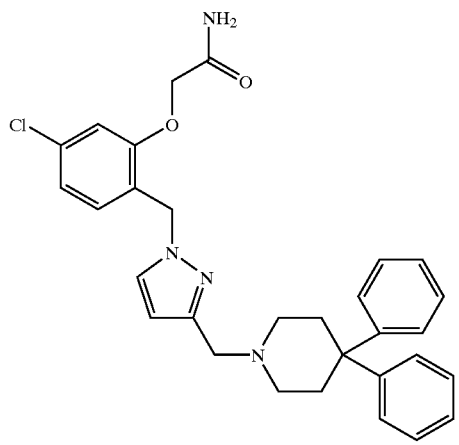

MS: APCI(+ve) base peak 515.

EXAMPLE 40

2-[5-Chloro-2-({3-[(4,4-diphenyl-1-piperidinyl)methyl]-1H-pyrazol-1-yl}methyl)phenoxy]-N,N-dimethylacetamide

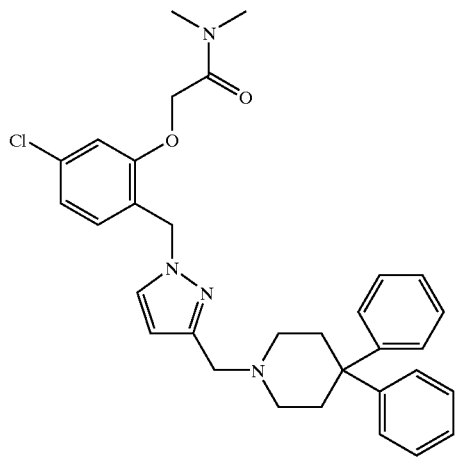

MS: APCI(+ve) base peak 543.

EXAMPLE 41

2-[5-Chloro-2-({3-[(4,4-diphenyl-1-piperidinyl)methyl]-1H-pyrazol-1-yl}methyl)phenoxy]-N,N-diethylacetamide

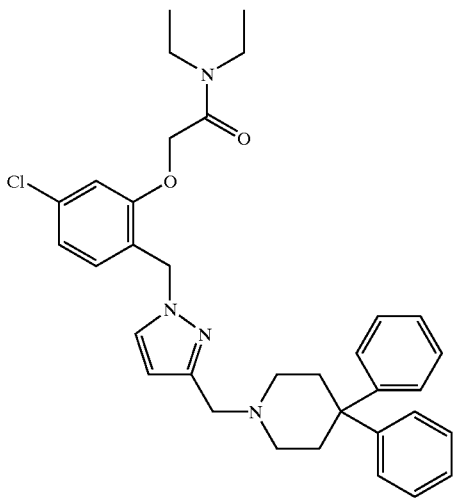

MS: APCI(+ve) base peak 571.

EXAMPLE 42

2-[5-Chloro-2-({3-[(4,4-diphenyl-1-piperidinyl)methyl]-1H-pyrazol-1-yl}methyl)phenoxy]propanamide

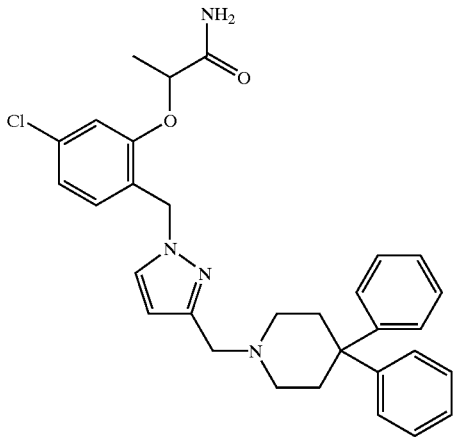

MS: APCI(+ve) base peak 529.

EXAMPLE 43

2-[5-Chloro-2-({3-[(4,4-diphenyl-1-piperidinyl)methyl]-1H-pyrazol-1-yl}methyl)phenoxy]-N-methylacetamide

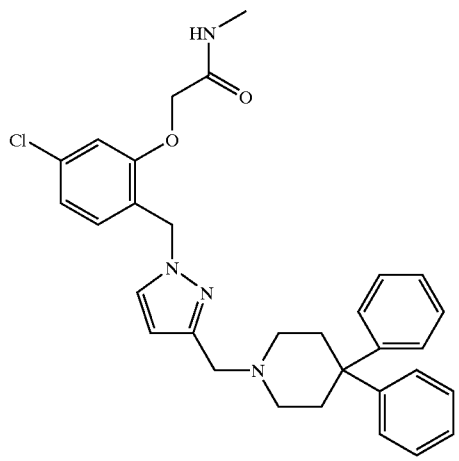

MS: APCI(+ve) base peak 529.

EXAMPLE 44

1-{2-[5-Chloro-2-({3-[(4,4-diphenyl-1-piperidinyl)methyl]-1H-pyrazol-1-yl}methyl)phenoxy]acetyl}-3-pyrazolidinone

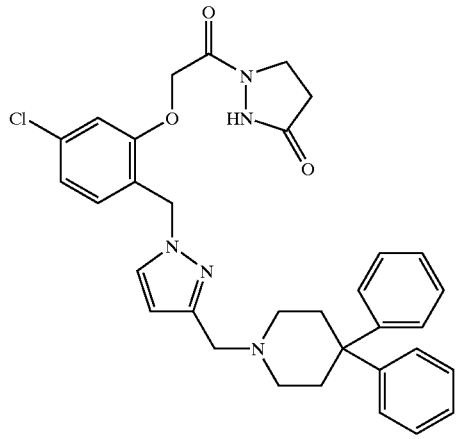

MS: APCI(+ve) base peak 584.

EXAMPLE 45

1-[(1-{4-Chloro-2-[(3,5-dimethyl-4-isoxazolyl)methoxy]benzyl}-1H-pyrazol-3-yl)methyl]-4,4-diphenylpiperidine

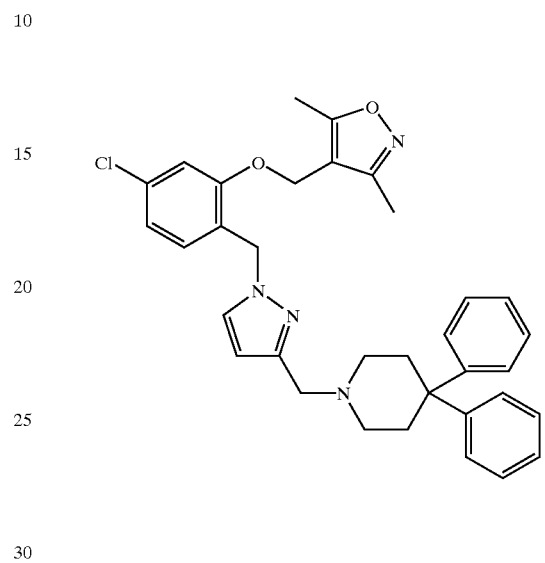

MS: APCI(+ve) base peak 567.

EXAMPLE 46

5-Chloro-2-({3-[(4,4-diphenyl-1-piperidinyl)methyl]-1H-pyrazol-1-yl}methyl)phenyl(1-methyl-1H-imidazol-2-yl)methyl Ether

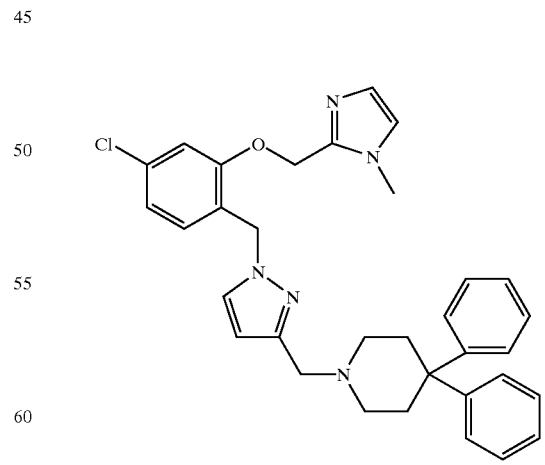

MS: APCI(+ve) base peak 552.

EXAMPLE 47

5-Chloro-2-({3-[(4,4-diphenyl-1-piperidinyl)methyl]-1H-pyrazol-1-yl}methyl)phenyl(2-methyl-1,3-thiazol-4-yl)methyl Ether

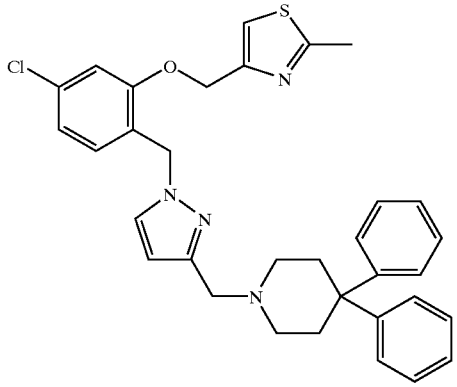

MS: APCI(+ve) base peak 569.

Following the general method of Example 20 and using the appropriate amine, the compounds of Examples 48 to 94 were prepared.

EXAMPLE 48

{1-(4-Chlorobenzyl)-4-[(4,4-diphenyl-1-piperidinyl)methyl]-1H-imidazol-5-yl}(4-mompholinyl)methanone

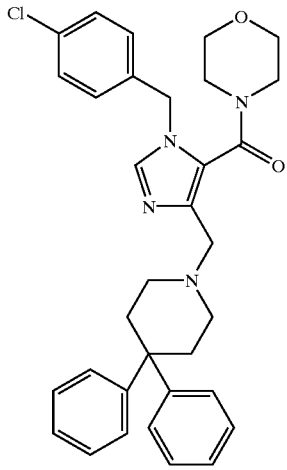

MS: APCI(+ve) base peak 555.

EXAMPLE 49

1-(4-Chlorobenzyl)-4-[(4,4-diphenyl-1-piperidinyl)methyl]-N,N-dimethyl-1H-imidazole-5-carboxamide

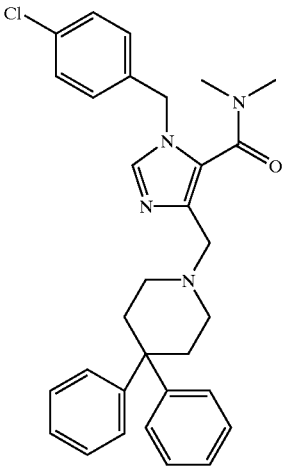

MS: APCI(+ve) base peak 513.

EXAMPLE 50

1-(4-Chlorobenzyl)-4-[(4,4-diphenyl-1-piperidinyl)methyl]-N-(2-methoxyethyl)-1H-imidazole-5-carboxamide

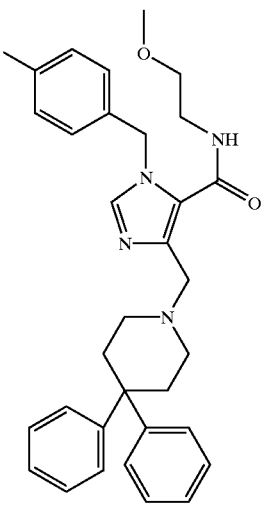

MS: APCI(+ve) base peak 552.

EXAMPLE 51

1-(4-Chlorobenzyl)-4-[(4,4-diphenyl-1-piperidinyl)methyl]-N-(4-hydroxycyclohexyl)-1H-imidazole-5-carboxamide

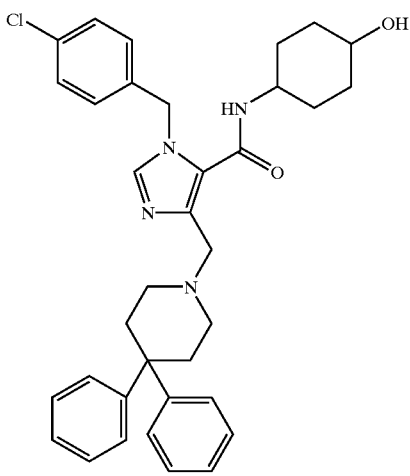

MS: APCI(+ve) base peak 543.

EXAMPLE 52

1-(4-Chlorobenzyl)-4-[(4,4-diphenyl-1-piperidinyl)methyl]-N-[1-(hydroxymethyl)propyl]-1H-imidazole-5-carboxamide

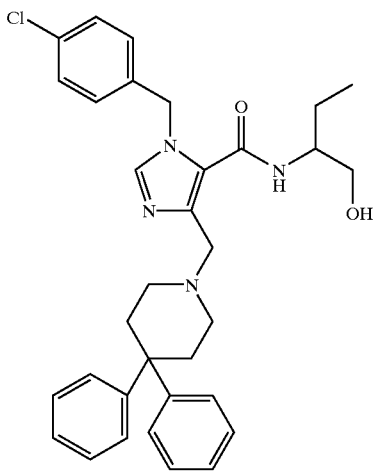

MS: APCI(+ve) base peak 557.

EXAMPLE 53

1-(4-Chlorobenzyl)-4-[(4,4-diphenyl-1-piperidinyl)methyl]-N-(tetrahydro-2-furanylmethyl)-1H-imidazole-5-carboxamide

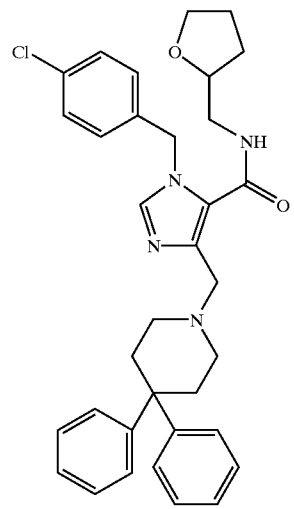

MS: APCI(+ve). base peak 569.

EXAMPLE 54

{1-(4-Chlorobenzyl)-4-[(4,4-diphenyl-1-piperidinyl)methyl]-1H-imidazol-5-yl}[2-(hydroxymethyl)-1-piperidinyl]methanone

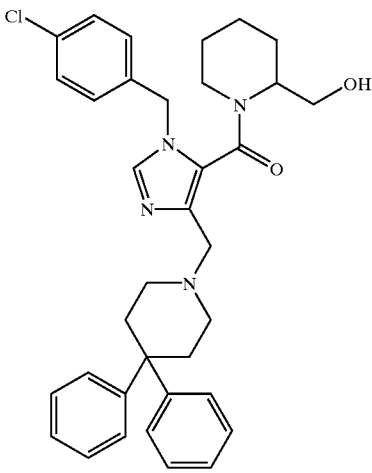

MS: APCI(+ve) base peak 583.

EXAMPLE 55

1-(4-Chlorobenzyl)-N-[3-(diethylamino)propyl]-4-[(4,4-diphenyl-1-piperidinyl)methyl]-1H-imidazole-5-carboxamide

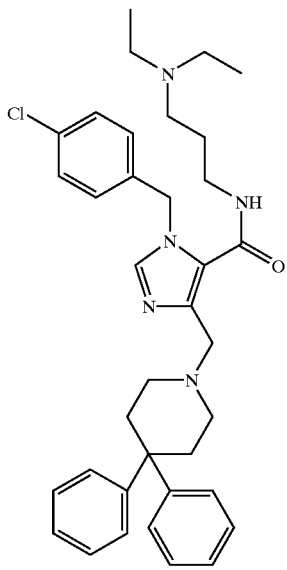

MS: APCI(+ve) base peak 598.

EXAMPLE 56

{1-(4-Chlorobenzyl)-4-[(4,4-diphenyl-1-piperidinyl)methyl]-1H-imidazol-5-yl}[3-(hydroxymethyl)-1-piperidinyl]methanone

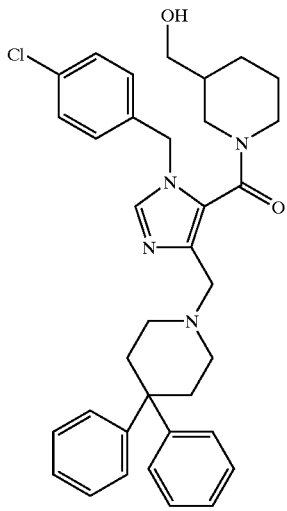

MS: APCI(+ve) base peak 583.

EXAMPLE 57

1-(4-Chlorobenzyl)-4-[(4,4-diphenyl-1-piperidinyl)methyl]-N-(2-hydroxyethyl)-1H-imidazole-5-carboxamide

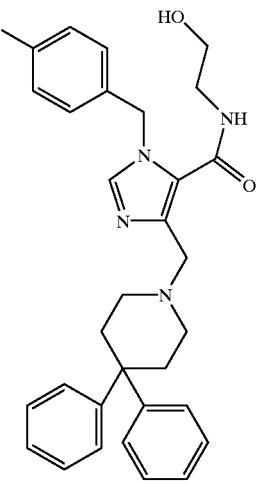

MS: APCI(+ve) base peak 529.

EXAMPLE 58

1-(4-Chlorobenzyl)-4-[(4,4-diphenyl-1-piperidinyl)methyl]-N-(2-hydroxyethyl)-N-methyl-1H-imidazole-5-carboxamide

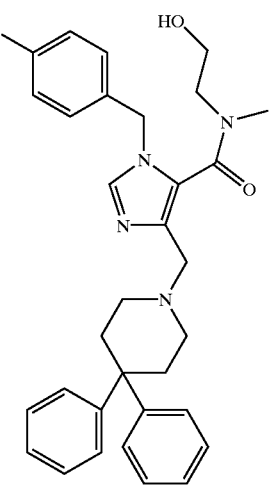

MS: APCI(+ve) base peak 543.

EXAMPLE 59

1-(4-Chlorobenzyl)-4-[(4,4-diphenyl-1-piperidinyl)methyl]-N-[3-(1H-imidazol-1-yl)propyl]-1H-imidazole-5-carboxamide

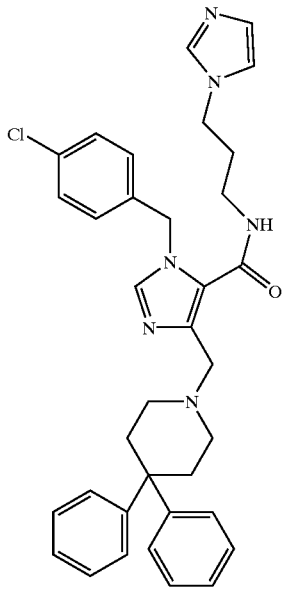

MS: APCI(+ve) base peak 593.

EXAMPLE 60

{1-(4-Chlorobenzyl)-4-[(4,4-diphenyl-1-piperidinyl)methyl]-1H-imidazol-5-yl}(1-pyrrolidinyl)methanone

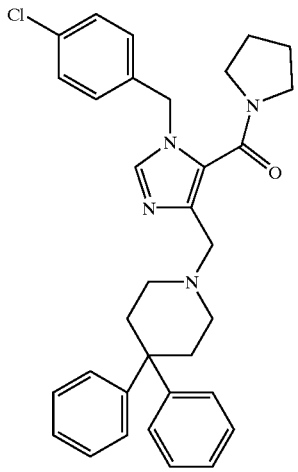

MS: APCI(+ve) base peak 539.

EXAMPLE 61

{1-(4-Chlorobenzyl)-4-[(4,4-diphenyl-1-piperidinyl)methyl]-1H-imidazol-5-yl}(3-hydroxy-1-pyrrolidinyl)methanone

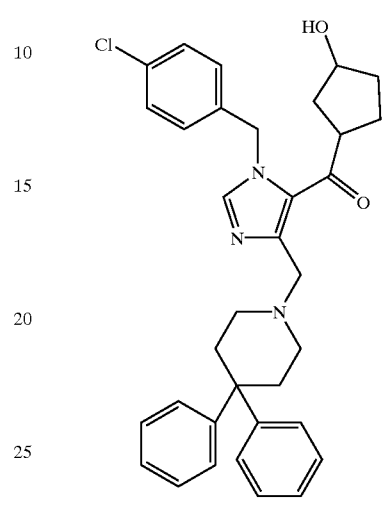

MS: APCI(+ve) base peak 555.

EXAMPLE 62

1-[4-({1-(4-Chlorobenzyl)-4-[(4,4-diphenyl-1-piperidinyl)methyl]-1H-imidazol-5-yl}carbonyl)-1-piperazinyl]-1-ethanone

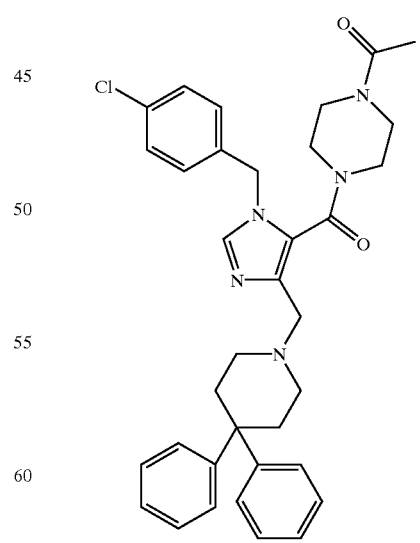

MS: APCI(+ve) base peak 596.

EXAMPLE 63

{1-(4-Chlorobenzyl)-4-[(4,4-diphenyl-1-piperidinyl)methyl]-1H-imidazol-5-yl}(1-piperidinyl)methanone

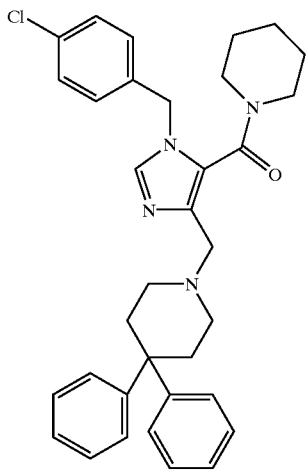

MS: APCI(+ve) base peak 553.

EXAMPLE 64

1-(4-Chlorobenzyl)-N-[2-(diethylamino)ethyl]-4-[(4,4-diphenyl-1-piperidinyl)methyl]-N-(2hydroxyethyl)-1H-imidazole-5-carboxamide

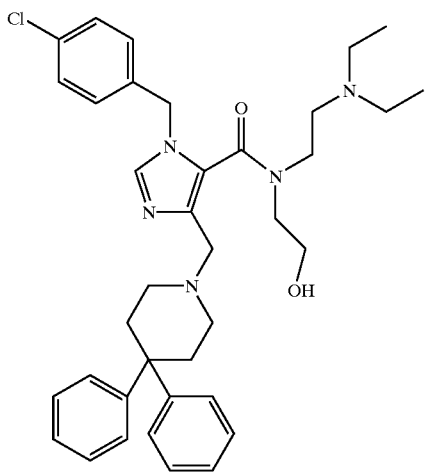

MS: APCI(+ve) base peak 628.

EXAMPLE 65

1-(4-Chlorobenzyl)-4-[(4,4-diphenyl-1-piperidinyl)methyl]-N-[2-(4-morpholinyl)ethyl]-1H-imidazole-5-carboxamide

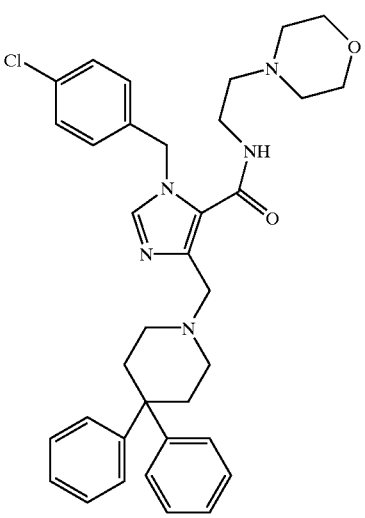

MS: APCI(+ve) base peak 598.

EXAMPLE 66

1-(4-Chlorobenzyl)-4-[(4,4-diphenyl-1-piperidinyl)methyl]-N-ethyl-N-(2-hydroxyethyl)-1H-imidazole-5-carboxamide

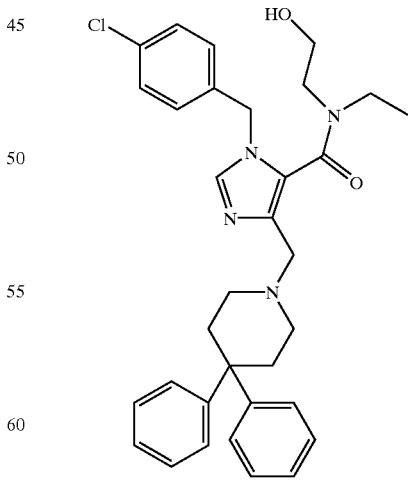

MS: APCI(+ve) base peak 587.

EXAMPLE 67

{1-(4-Chlorobenzyl)-4-[(4,4-diphenyl-1-piperidinyl)methyl]-1H-imidazol-5-yl}(4-ethyl-1-piperazinyl)methanone

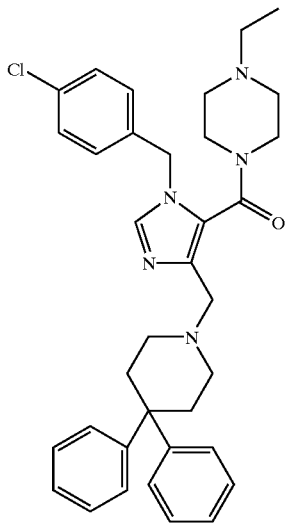

MS: APCI(+ve) base peak 582.

EXAMPLE 68

N-(2-Amino-2-oxoethyl)-1-(4-chlorobenzyl)-4-[(4,4-diphenyl-1-piperidinyl)methyl]-1H-imidazole-5-carboxamide

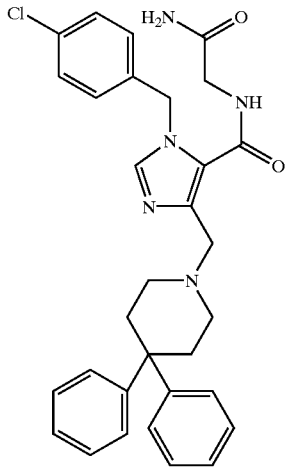

MS: APCI(+ve) base peak 542.

EXAMPLE 69

1-(4-Chlorobenzyl)-4-[(4,4-diphenyl-1-piperidinyl)methyl]-N-[2-(1-pyrrolidinyl)ethyl]-1H-imidazole-5-carboxamide

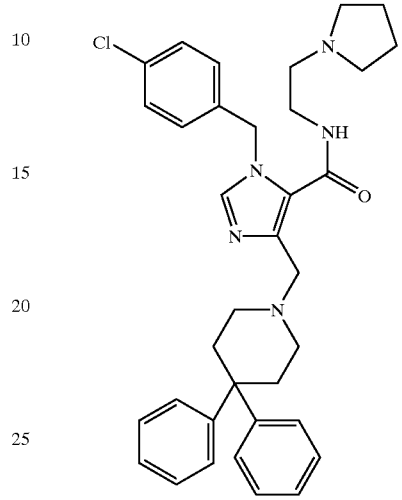

MS: APCI(+ve) base peak 582.

EXAMPLE 70

1-(4-Chlorobenzyl)-4-[(4,4-diphenyl-1-piperidinyl)methyl]-N-[2-(1H-imidazol-4-yl)ethyl]-1H-imidazole-5-carboxamide

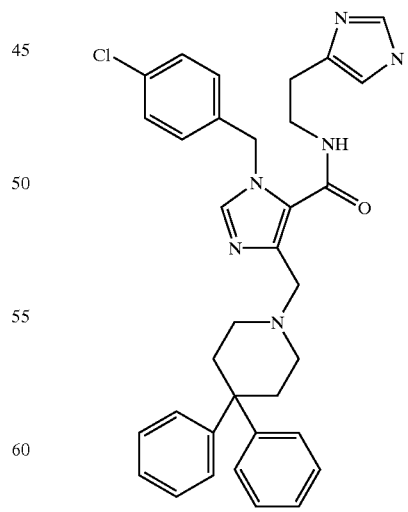

MS: APCI(+ve) base peak 579.

EXAMPLE 71

1-(4-Chlorobenzyl)-4-[(4,4-diphenyl-1-piperidinyl)methyl]-N-methyl-1H-imidazole-5-carboxamide

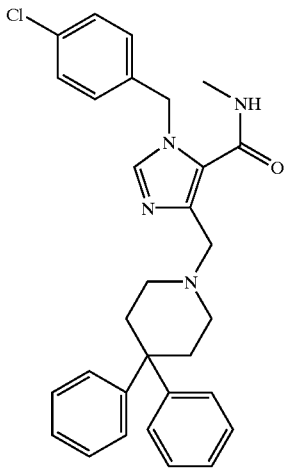

MS: APCI(+ve) base peak 499.

EXAMPLE 72

1-(4-Chlorobenzyl)-N-(2,3-dihydroxypropyl)-4-[(4,4-diphenyl-1-piperidinyl)methyl]-1H-imidazole-5-carboxamide

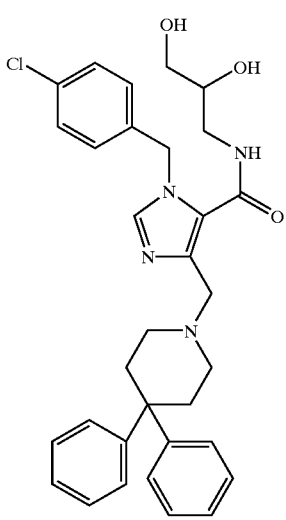

MS: APCI(+ve) base peak 559.

EXAMPLE 73

1-(4-Chlorobenzyl)-4-[(4,4-diphenyl-1-piperidinyl)methyl]-N-[(1-ethyl-2-pyrrolidinyl)methyl]-1H-imidazole-5-carboxamide

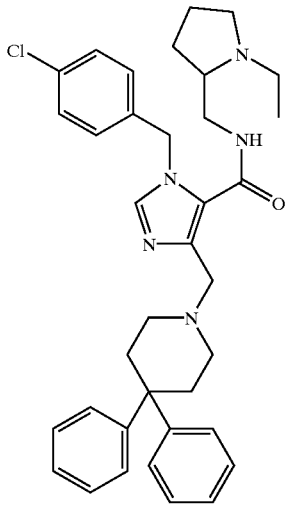

MS: APCI(+ve) base peak 596.

EXAMPLE 74

Ethyl 1-({1-(4-Chlorobenzyl)-4-[(4,4-diphenyl-1-piperidinyl)methyl]-1H-imidazol-5-yl}carbonyl)-4-piperidinecarboxylate

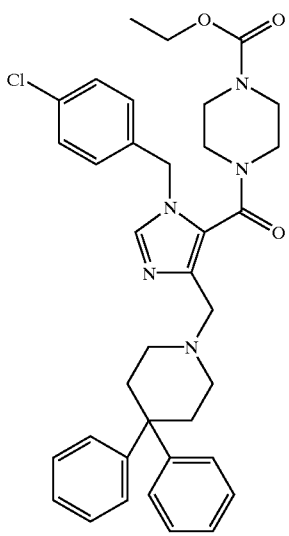

MS: APCI(+ve) base peak 625.

EXAMPLE 75

Ethyl 1-({1-(4-Chlorobenzyl)-4-[(4,4-diphenyl-1-piperidinyl)methyl]-1H-imidazol-5-yl}carbonyl)-3-piperidinecarboxylate

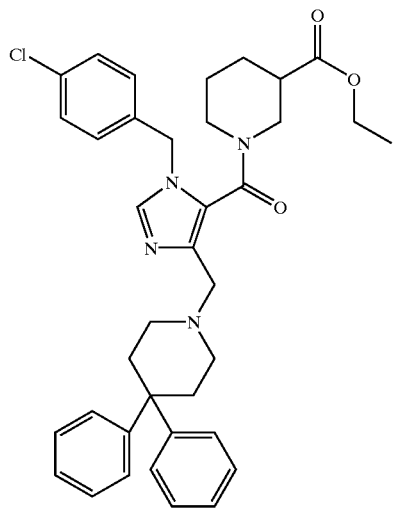

MS: APCI(+ve) base peak 625.

EXAMPLE 76

Methyl 3-[({1-(4-chlorobenzyl)-4-[(4,4-diphenyl-1-piperidinyl)methyl]-1H-imidazol-5-yl}carbonyl)amino]propanoate

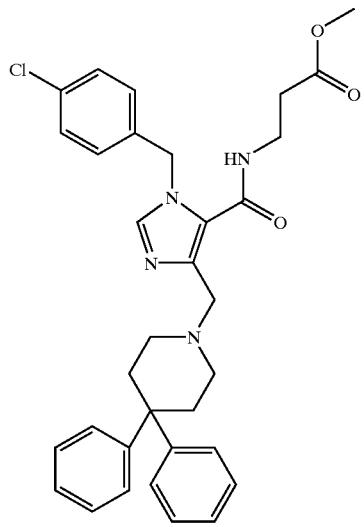

MS: APCI(+ve) base peak 571.

EXAMPLE 77

Methyl 2-[({1-(4-Chlorobenzyl)-4-[(4,4-diphenyl-1-piperidinyl)methyl]-1H-imidazol-5-yl}carbonyl)amino]acetate

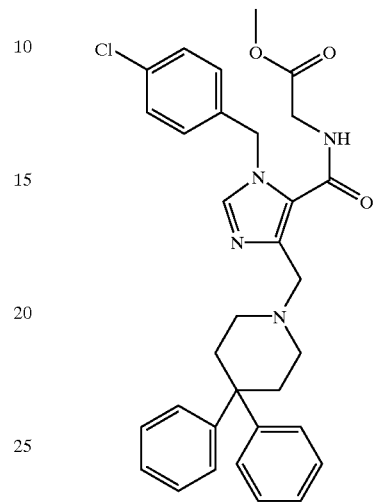

MS: APCI(+ve) base peak 557.

EXAMPLE 78

1-(4-Chlorobenzyl)-4-[(4,4-diphenyl-1-piperidinyl)methyl]-N-(2-pyridinylmethyl)-1H-imidazole-5-carboxamide

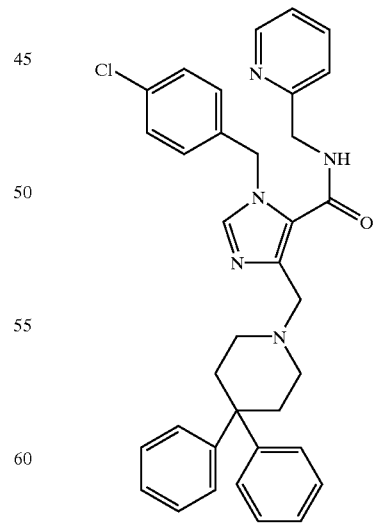

MS: APCI(+ve) base peak 576.

EXAMPLE 79

1-(4-Chlorobenzyl)-4-[(4,4-diphenyl-1-piperidinyl)methyl]-N-[2-(2-pyridinyl)ethyl]-1H-imidazole-5-carboxamide

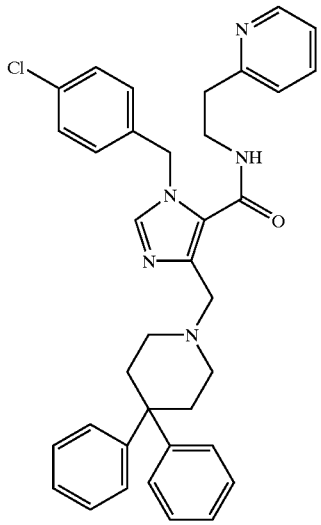

MS: APCI(+ve) base peak 590.

EXAMPLE 80

1-(4-Chlorobenzyl)-4-[(4,4-diphenyl-1-piperidinyl)methyl]-N-(3-pyridinylmethyl)-1H-imidazole-5-carboxamide

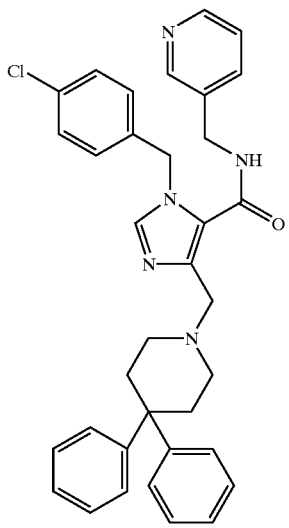

MS: APCI(+ve) base peak 576.

EXAMPLE 81

1-(4-Chlorobenzyl)-4-[(4,4-diphenyl-1-piperidinyl)methyl]-N-(2-hydroxy-1,1-dimethylethyl)-1H-imidazole-5-carboxamide

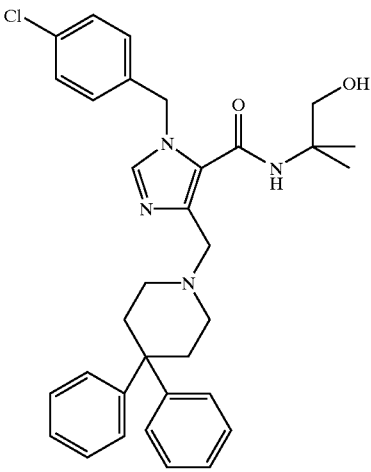

MS: APCI(+ve) base peak 557.

EXAMPLE 82

1-(4-Chlorobenzyl)-4-[(4,4-diphenyl-1-piperidinyl)methyl]-N-(2-hydroxy-1-methylethyl)-1H-imidazole-5-carboxamide

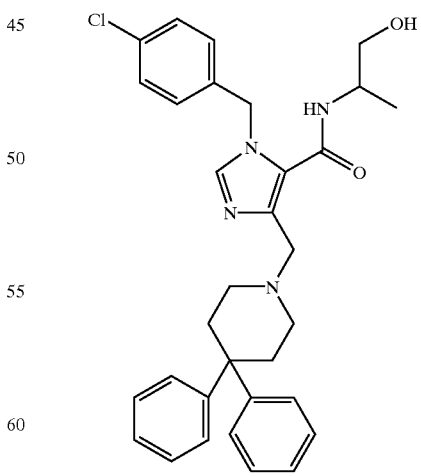

MS: APCI(+ve) base peak 543.

EXAMPLE 83

1-(4-Chlorobenzyl)-4-[(4,4-diphenyl-1-piperidinyl)methyl]-N-[3-(2-oxo-1-pyrrolidinyl)propyl]-1H-imidazole-5-carboxamide

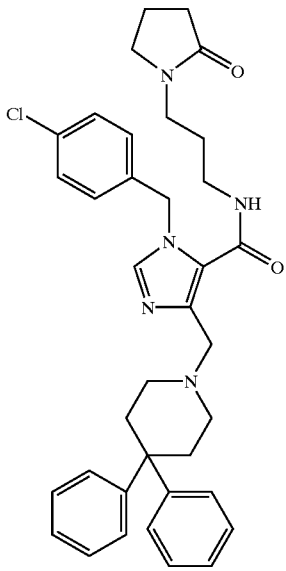

MS: APCI(+ve) base peak 610.

EXAMPLE 84

N-[2-(Acetylamino)ethyl]-1-(4-chlorobenzyl)-4-[(4,4-diphenyl-1-piperidinyl)methyl]-1H-imidazole-5-carboxamide

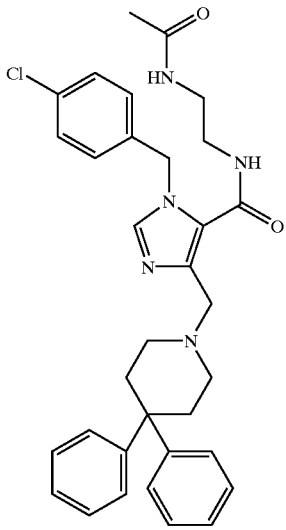

MS: APCI(+ve) base peak 570.

EXAMPLE 85

1-(4-Chlorobenzyl)-4-[(4,4-diphenyl-1-piperidinyl)methyl]-N-[2-(2-hydroxyethoxy)ethyl]-1H-imidazole-5-carboxamide

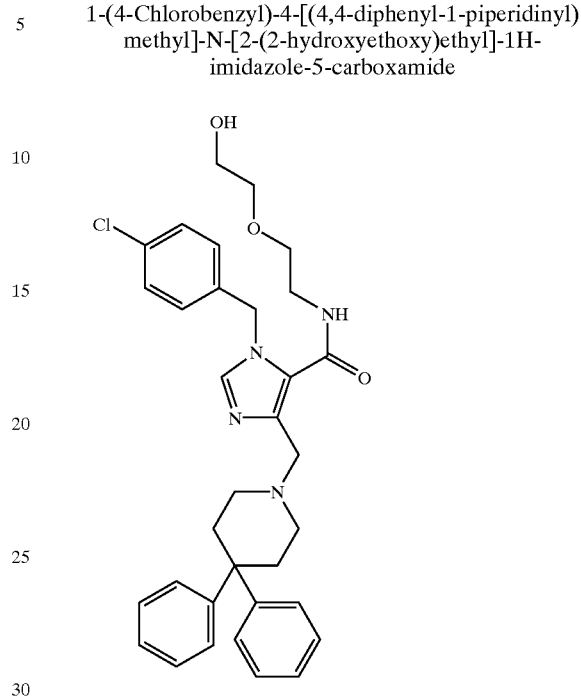

MS: APCI(+ve) base peak 573.

EXAMPLE 86

1-(4-Chlorobenzyl)-4-[(4,4-diphenyl-1-piperidinyl)methyl]-N-[1-(hydroxymethyl)cyclopentyl]-1H-imidazole-5-carboxamide

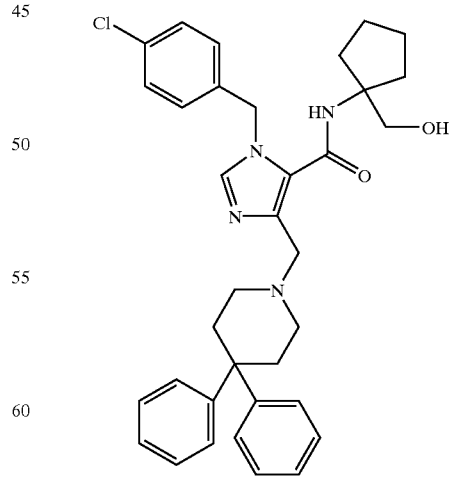

MS: APCI(+ve) base peak 583.

EXAMPLE 87

1-(4-Chlorobenzyl)-4-[(4,4-diphenyl-1-piperidinyl)methyl]-N-[2-hydroxyl-1-(hydroxymethyl)ethyl]-1H-imidazole-5-carboxamide

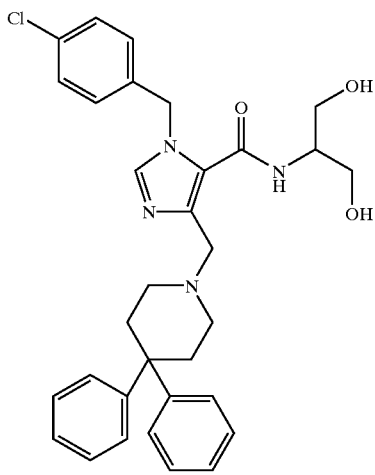

MS: APCI(+ve) base peak 559.

EXAMPLE 88

1-(4-Chlorobenzyl)-4-[(4,4-diphenyl-1-piperidinyl)methyl]-N-(3-methoxypropyl)-1H-imidazole-5-carboxamide

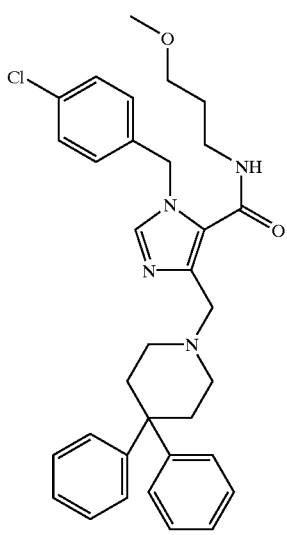

MS: APCI(+ve) base peak 557.

EXAMPLE 89

1-({1-(4-Chlorobenzyl)-4-[(4,4-diphenyl-1-piperidinyl)methyl]-1H-imidazol-5-yl}carbonyl)-2-pyrrolidinecarboxamide

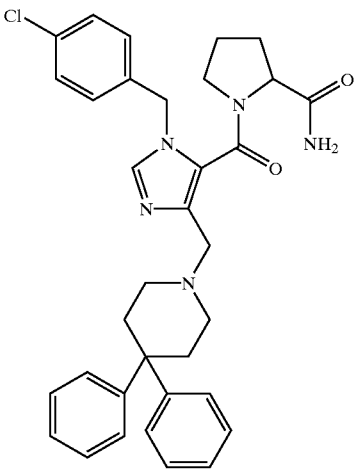

MS: APCI(+ve) base peak 582.

EXAMPLE 90

1-({1-(4-Chlorobenzyl)-4-[(4,4-diphenyl-1-piperidinyl)methyl]-1H-imidazol-5-yl}carbonyl)-2-pyrrolidinecarboxamide

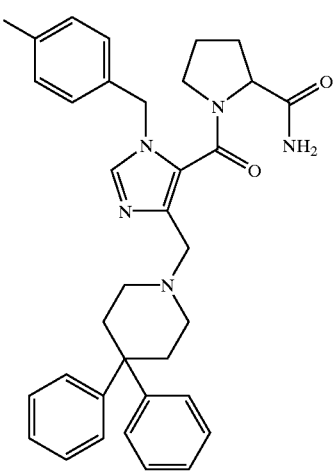

MS: APCI(+ve) base peak 582.

EXAMPLE 91

{1-(4-Chlorobenzyl)-4-[(4,4-diphenyl-1-piperidinyl)methyl]-1H-imidazol-5-yl}[4-(2-hydroxyethyl)-1-piperidinyl]methanone

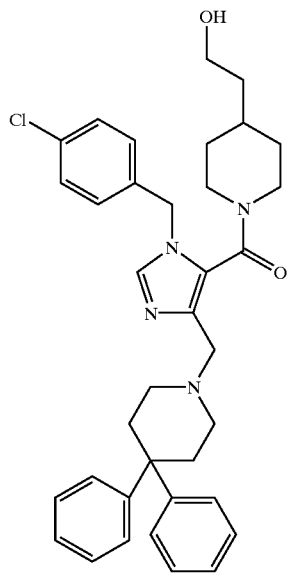

MS: APCI(+ve) base peak 597.

EXAMPLE 92

1-(4-Chlorobenzyl)-4-[(4,4-diphenyl-1-piperidinyl)methyl]-N-(2-propynyl)-1H-imidazole-5-carboxamide

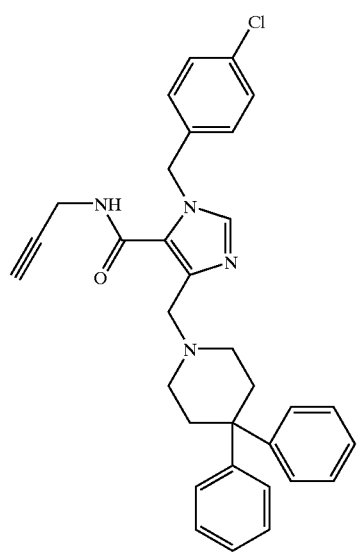

MS: APCI(+ve) base peak 523.

EXAMPLE 93

4-({1-(4-Chlorobenzyl)-4-[(4,4-diphenyl-1-piperidinyl)methyl]-1H-imidazol-5-yl}carbonyl)-2-piperazinone

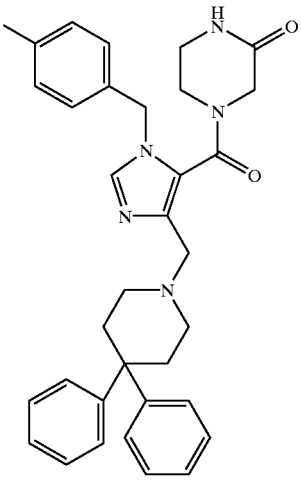

MS: APCI(+ve) base peak 513.

EXAMPLE 94

1-(4-Chlorobenzyl)-4-[(4,4-diphenyl-1-piperidinyl)methyl]-N-[1-(hydroxymethyl)propyl]-1H-imidazole-5-carboxamide

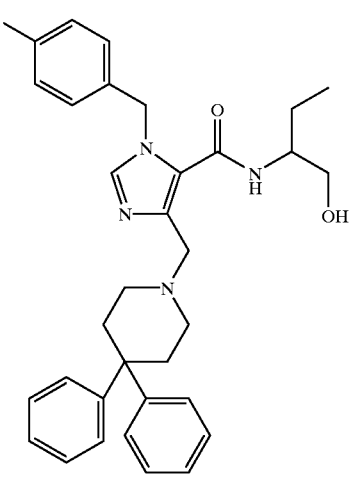

MS: APCI(+ve) base peak 557.

EXAMPLE 95

1-{3-(4-Chlorobenzyl)-[1,2,4]oxadiazol-5-ylmethyl}-4,4-diphenylpiperidine Hydrochloride

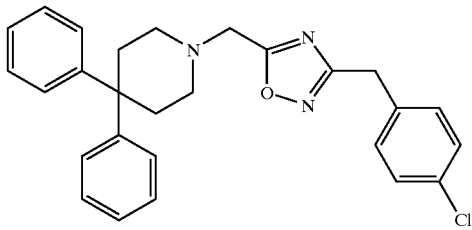

(a) 3-(4-Chlorobenzyl)-1,2,4]oxadiazole-5-methanol

To a stirred suspension of 4-chloro-N-hydroxy-benzeneethanimidamide (3.0 g) and potassium carbonate (2.46 g) in acetone (60 ml) at 0° C. was added a solution of acetoxyacetylchloride (1.75 ml). After 2 hours the solution was allowed to warm to room temperature, water and dichloromethane were added, the organic phase was separated and concentrated. The residue was dissolved in toluene (100 ml) and the solution heated under reflux for 20 hours, cooled and concentrated to an oil. Purification by chromatography (isohexane:ethyl acetate, 6:1) gave an oil (2.2 g) which was dissolved in methanol (20 ml) and potassium carbonate (1.15 g) added. The mixture was stirred at room temperature for 16 hours, water and ethyl acetate were added, the organic phase separated and the solvent removed to give an oil (1.6 g).

MS: APCI(+ve) 225/227 (M+H); $^1$H NMR δ (CDCl$_3$) 7.3–7.2 (m, 4H), 4.8 (s, 2H), 4.04 (s, 2H), 2.9 (s, 1H).

(b) 1-{3-(4-Chlorobenzyl)-[1,2,4]oxadiazol-5-ylmethyl}-4,4-diphenyl-piperidine Hydrochloride Using the method of Example 17(b), the product of Example 95(a) (0.5 g) gave the crude product as an oil. Purification by chromatography (isohexane:ethyl acetate, 3:1) gave a foam which upon treatment with 1.0M ethereal hydrogen chloride solution gave the title product as a solid (0.15 g), m.p. 161–162° C.

MS: ESI(+ve) 448.18 (M+H); $^1$H NMR δ (d$_6$-DMSO) 7.6–7.2 (m, 15H), 4.76 (s, 2H), 4.13(s, 2H), 3.05 (sb, 4H), 2.5 (sb, 4H).

Pharmacological Analysis

Calcium Flux [Ca$^{2+}$]$_i$ Assay a) Human Eosinophils

Human eosinophils were isolated from EDTA anticoagulated peripheral blood as previously described (Hansel et al., J. Immunol. Methods, 1991, 145, 105–110). The cells were resuspended (5×10$^6$ ml$^{-1}$) and loaded with 5 μM FLUO-3/AM+Pluronic F127 2.2 μl/ml (Molecular Probes) in low potassium solution (LKS; NaCl 118 mM, MgSO$_4$ 0.8 mM, glucose 5.5 mM, Na$_2$CO$_3$ 8.5 mM, KCl 5 mM, HEPES 20 mM, CaCl$_2$ 1.8 mM, BSA 0.1%, pH 7.4) for one hour at room temperature. After loading, cells were centrifuged at 200 g for 5 min and resuspended in LKS at 2.5×10 ml$^{-1}$. The cells were then transferred to 96 well FLIPr plates (Poly-D-Lysine plates from Becton Dickinson pre-incubated with 5 μM fibronectin for two hours) at 100 ml/well. The plate was centrifuged at 200 g for 5 min and the cells were washed twice with LKS (200 μl; room temperature).

A compound of the Examples was pre-dissolved in dimethylsulphoxide and added to a final concentration of 0.1% (v/v) dimethylsulphoxide. Assays were initiated by the addition of an A$_{50}$ concentration of eotaxin and the transient increase in fluo-3 fluorescence (1$_{Ex}$=490 nm and 1$_{Em}$=520 nm) monitored using a FLIPR (Fluorometric Imaging Plate Reader, Molecular Devices, Sunnyvale, U.S.A.).

b) Human Monocytes

Human monocytes were isolated from EDTA anticoagulated peripheral blood as previously described (Cunoosamy & Holbrook, J. Leukocyte Biology, 1998, S2, 13). Cells were resuspended (5×10$^6$ ml$^{-1}$) in LKS and loaded with 5 μM FLUO-3/AM+Pluronic F127 2.2 μl/ml (Molecular Probes) for one hour at room temperature. After loading, cells were centrifuged at 200 g for 5 min and resuspended in LKS at 0.5×10$^6$ ml$^{-1}$. The cells were then transferred to 96 well FLIPr plates (Costar). To each well 100 μl of cells were added at a concentration of 0.5×10$^6$ ml$^{-1}$. The plates were centrifuged (200 g; 5 mins; room temperature) to allow the cells to adhere. After centrifugation the cells were washed twice with LKS (200 μl; room temperature).

A compound of the Examples was pre-dissolved in dimethylsulphoxide and added to a final concentration of 0.1% (v/v) dimethylsulphoxide. Assays were initiated by the addition of an A$_{50}$ concentration of MIP-1α and the transient increase in fluo-3 fluorescence (1$_{Ex}$=490 nm and 1$_{Em}$=520 nm) monitored using a FLIPR (Fluorometric Imaging Plate Reader, Molecular Devices, Sunnyvale, U.S.A.).

The compounds of the Examples were found to be antagonists of the eotaxin mediated [Ca$^{2+}$]$_i$ in human eosinophils and/or antagonists of the MIP-1α mediated [Ca$^{2+}$]$_i$ in human monocytes.

Human Eosinophil Chemotaxis

Human eosinophils were isolated from EDTA anticoagulated peripheral blood as previously described (Hansel et al., J. Immunol. Methods, 1991, 145, 105–110). The cells were resuspended at 10×10$^6$ ml$^{-1}$ in RPMI containing 200 μU/ml penicillin, 200 μg/ml streptomycin sulphate and supplemented with 10% HIFCS, at room temperature.

Eosinophils (700 μl) were pre-incubated for 15 mins at 370° C. with 7 μl of either vehicle or compound (100× required final concentration in 10% dimethylsulphoxide). The chemotaxis plate (ChemoTx, 3 μm pore, Neuroprobe) was loaded by adding 28 μl of a concentration of eotaxin (0.1 to 100 nM) containing a concentration of a compound according to the Examples or solvent to the lower wells of the chemotaxis plate. The filter was then placed over the wells and 25 μl of eosinophil suspension were added to the top of the filter. The plate was incubated for 1 hr at 37° C. in a humidified incubator with a 95% air/5% CO$_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 μl of PBS containing 0.5% Tritonx100 followed by two cycles of freeze/thawing. The cell lysate was then added to the supernatant. The number of eosinophils migrating was quantified according to the method of Strath et al., J. Immunol. Methods, 1985, 83, 209 by measuring eosinophil peroxidase activity in the supernatant.

Certain compounds of the Examples were found to be antagonists of the eotaxin mediated human eosinophil chemotaxis.

What is claimed is:

1. A compound of formula (I)

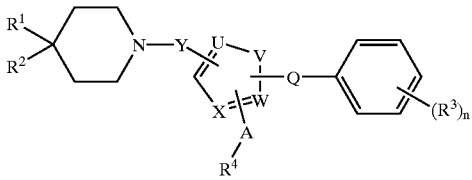

wherein:
- $R^1$ and $R^2$ independently represent phenyl optionally substituted by halogen, C1 to 6 alkyl, nitro, cyano, hydroxy, methylenedioxy, C1 to 6 alkoxy, C1 to 6 haloalkyl, C1 to 6 haloalkoxy or C1 to 6 alkylsulphonyl;
- each $R^3$ independently represents halogen, nitro, C1 to 6 alkyl, cyano, C1 to 6 haloalkyl, hydroxy or C1 to 6 alkoxy; each alkoxy group being optionally further substituted by halogen, $NR^5R^6$, $CO_2R^7$, $CONR^8R^9$, pyrazolidinone, or a five membered heteroaromatic ring incorporating one to three heteroatoms independently selected from N, O and S; said heteroaromatic ring being optionally further substituted by one or more C1 to 4 alkyl groups;
- n represents an interger 0 to 3;
- $R^4$ represents hydrogen, hydroxy or $NR^{10}R^{11}$;
- A represents —CO—, —CH$_2$— or a bond;
- Q represents C1 to 4 alkylene;
- U, W and X independently represent carbon, optionally substituted by C1 to 4 alkyl, or nitrogen;
- V represents nitrogen, optionally substituted by C1 to 4 alkyl, or oxygen;
- Y represents C1 to 4 alkylene or —CO—;
- $R^5$, $R^6$, $R^7$, $R^8$, $R^9$ independently represent hydrogen or C1 to 6 alkyl;
- $R^{10}$ and $R^{11}$ independently represent hydrogen, C2 to 6 unsaturated alkyl or C1 to 6 alkyl; each alkyl group being optionally further substituted by $CO_2R^{12}$, hydroxy, C1 to 6 alkoxy, $CONH_2$, $NR^{13}R^{14}$, $OCH_2CH_2OH$, or a five or six membered saturated or unsaturated heterocyclic ring containing one or two heteroatoms selected from N, O and S; said ring optionally comprising one ring carbon atom that forms a carbonyl group; and said ring being optionally further substituted by C1 to 4 alkyl;
- or the group $NR^{10}R^{11}$ together represents a 4 to 8 membered saturated azacyclic ring system; said ring optionally comprising one additional ring heteroatom selected from N, O and S, said ring optionally comprising one ring carbon atom that forms a carbonyl group; and said ring being optionally further substituted by C1 to 6 alkyl, C1 to 6 hydroxyalkyl, hydroxy, $CO_2R^{15}$, $CONH_2$, CHO or $COCH_3$;
- $R^{12}$ and $R^{15}$ independently represent hydrogen or C1 to 4 alkyl; and
- $R^{13}$ and $R^{14}$ independently represent hydrogen, C1 to 4 alkyl or C1 to 4 alkanoyl;

or a pharmaceutically acceptable salt or solvate thereof.

2. A compound according to claim 1 wherein V represents nitrogen.

3. A compound according to claim 1, wherein $R^3$ represents halogen.

4. A compound according to claim 3, wherein $R^3$ represents chlorine.

5. A compound of formula (I), or a pharmaceutically acceptable salt or solvate thereof, according to claim 1 being selected from:
- 1-[(1-benzyl)-1H-pyrazol-3-yl]methyl]-4,4-diphenylpiperidine;
- 1-{[-(3-chlorobenzyl)-1H-pyrazol-3-yl]methyl}-4,4-diphenylpiperidine;
- 1-{[1-(3,4-dimethylbenzyl)-1H-pyrazol-3-yl]methyl}-4,4-diphenylpiperidine;
- 1-{[1-(4-methylbenzyl)-1H-pyrazol-3-yl]methyl}-4,4-diphenylpiperidine;
- 4,4-diphenyl-1-({1-[4-(trifluoromethyl)benzyl]-1H-pyrazol-3-yl}methyl)piperidine;
- 1-{[1-(2,4-dichlorobenzyl)-1H-pyrazol-3-yl]methyl}-4,4-diphenylpiperidine;
- 1-{[1-(3,4-dichlorobenzyl)-1H-pyrazol-3-yl]methyl}-4,4-diphenylpiperidine;
- 1-{[1-(3,4-difluorobenzyl)-1H-pyrazol-3-yl]methyl}-4,4-diphenylpiperidine;
- 1-{[1-(4-chlorobenzyl)-1H-pyrazol-3-yl]methyl}-4,4-diphenylpiperidine;
- 1-{[1-(4-fluorobenzyl)-1H-pyrazol-3-yl]methyl}-4,4-diphenylpiperidine;
- 1-{[1-(4-chloro-2-methoxybenzyl)-1H-pyrazol-3-yl]methyl}-4,4-diphenylpiperidine;
- 5-chloro-2-({3[(4,4-diphenyl-1-piperidinyl)methyl]-1H-pyrazol-1-yl}methyl)phenol;
- 2-[5-chloro-2-({3-[(4,4-diphenyl-1-piperidinyl)methyl]-1H-pyrazol-1-yl}methyl)phenoxy]-N,N-dimethylacetamide;
- 1-{[1-(4-chlorobenzyl)-1H-imidazol-4-yl]methyl}-4,4-diphenylpiperidine;
- 1-(4-chlorobenzyl)-3-[(4,4-diphenyl-1-piperidinyl)methyl]-1H-pyrazole-4-carbaldehyde;
- {1-(4-chlorobenzyl)-3-[(4,4-diphenyl-1-piperidinyl)methyl]-1H-pyrazol-4-yl}methanol;
- 1-{[1-(4-chlorobenzyl)-1H-1,2,3-triazol-5-yl]methyl}-4,4-diphenylpiperidine;
- 1-{[1-(4-chlorobenzyl)-1H-1,2,3-triazol-4-yl]methyl}-4,4-diphenylpiperidine;
- 1-(4-chlorobenzyl)-4-[(4,4-diphenyl-1-piperidinyl)methyl]-1H-imidazole-5-carboxylic acid;
- 1-(4-chlorobenzyl)-4-[(4,4-diphenyl-1-piperidinyl)methyl]-1H-imidazole-5-carboxamide;
- 1-{[2-(4-chlorobenzyl)-1H-imidazol-5-yl]methyl}-4,4-diphenylpiperidine;
- 1-{[2-(4-chlorobenzyl)-1-methyl-1H-imidazol-5-yl]methyl}-4,4-diphenylpiperidine;
- 1-{[2-(4-chlorobenzyl)-3-methyl-3H-imidazol-5-yl]methyl}-4,4-diphenylpiperidine;
- [2-(4-chlorobenzyl)-1H-imidazol-5-yl](4,4-diphenyl-1-piperidinyl)methanone;
- 2-[4-({1-(4-chlorobenzyl)-3-[(4,4-diphenyl-1-piperidinyl)methyl]-1H-pyrazol-4-yl}methyl)-1-piperazinyl]-1-ethanol;
- 4-({1-(4-chlorobenzyl)-3-[(4,4-diphenyl-1-piperidinyl)methyl]-1H-pyrazol-4-yl}methyl)-1-piperazinecarbaldehyde;
- 1-[4-({1-(4-chlorobenzyl)-3-[(4,4-diphenyl-1-piperidinyl)methyl]-1H-pyrazol-4-yl}methyl)-1-piperazinyl]-1-ethanone;

$N^1$-({1-(4-chlorobenzyl)-3-[(4,4-diphenyl-1-piperidinyl)methyl]-1H-pyrazol-4-yl}methyl)-$N^1$,$N^2$,$N^2$-trimethyl-1,2-ethanediamine;

N-({1-(4-chlorobenzyl)-3-[(4,4-diphenyl-1-piperidinyl)methyl]-1H-pyrazol-4-yl}methyl)-2-(4-morpholinyl)-1-ethanamine;

1-{[4-(1-azetidinylmethyl)-1-(4-chlorobenzyl)-1H-pyrazol-3-yl]methyl}-4,4-diphenylpiperidine;

N-({1-(4-chlorobenzyl)-3-[(4,4-diphenyl-1-piperidinyl)methyl]-1H-pyrazol-4-yl}methyl)-2-(1-pyrrolidinyl)-1-ethanamine;

N-({1-(4-chlorobenzyl)-3-[(4,4-diphenyl-1-piperidinyl)methyl]-1H-pyrazol-4-yl}methyl)-beta-alanine;

2-[({1-(4-chlorobenzyl)-3-[(4,4-diphenyl-1-piperidinyl)methyl]-1H-pyrazol-4-yl}methyl)amino]acetic acid;

N-({1-(4-chlorobenzyl)-3-[(4,4-diphenyl-1-piperidinyl)methyl]-1H-pyrazol-4-yl}methyl)-2-(2-pyridinyl)-1-ethanamine;

{1-(4-chlorobenzyl)-3-[(4,4-diphenyl-1-piperidinyl)methyl]-1H-pyrazol-4-yl}-N-(4-pyridinylmethyl)methanamine;

2-[1-({1-(4-chlorobenzyl)-3-[(4,4-diphenyl-1-piperidinyl)methyl]-1H-pyrazol-4-yl}methyl)-4-piperidinyl]-1-ethanol;

1-({1-(4-chlorobenzyl)-3-[(4,4-diphenyl-1-piperidinyl)methyl]-1H-pyrazol-4-yl}methyl)-4-methyl-1,4-diazepane;

3-[5-chloro-2-({3-[(4,4-diphenyl-1-piperidinyl)methyl]-1H-pyrazol-1-yl}methyl)phenoxy]-N,N-dimethyl-1-propanamine;

2-[5-chloro-2-({3-[(4,4-diphenyl-1-piperidinyl)methyl]-1H-pyrazol-1-yl}methyl)phenoxy]acetic acid;

2-[5-chloro-2-({3-[(4,4-diphenyl-1-piperidinyl)methyl]-1H-pyrazol-1-yl}methyl)phenoxy]acetamide;

2-[5-chloro-2-({3-[(4,4-diphenyl-1-piperidinyl)methyl]-1H-pyrazol-1-yl}methyl)phenoxy]-N,N-dimethylacetamide;

2-[5-chloro-2-({3-[(4,4-diphenyl-1-piperidinyl)methyl]-1H-pyrazol-1-yl}methyl)phenoxy]-N,N-diethylacetamide;

2-[5-chloro-2-({3-[(4,4-diphenyl-1-piperidinyl)methyl]-1H-pyrazol-1-yl}methyl)phenoxy]propanamide;

2-[5-chloro-2-({3-[(4,4-diphenyl-1-piperidinyl)methyl]-1H-pyrazol-1-yl}methyl)phenoxy]-N-methylacetamide;

1-{2-[5-chloro-2-({3-[(4,4-diphenyl-1-piperidinyl)methyl]-1H-pyrazol-1-yl}methyl)phenoxy]acetyl}-3-pyrazolidinone;

1-[(1-{4-chloro-2-[(3,5-dimethyl-4-isoxazolyl)methoxy]benzyl}-1H-pyrazol-3-yl)methyl]-4,4-diphenylpiperidine;

5-chloro-2-({3-[(4,4-diphenyl-1-piperidinyl)methyl]-1H-pyrazol-1-yl}methyl)phenyl (1-methyl-1H-imidazol-2-yl)methyl ether;

5-chloro-2-({3-[(4,4-diphenyl-1-piperidinyl)methyl]-1H-pyrazol-1-yl}methyl)phenyl (2-methyl-1,3-thiazol-4-yl)methyl ether;

{1-(4-chlorobenzyl)-4-[(4,4-diphenyl-1-piperidinyl)methyl]-1H-imidazol-5-yl}(4-morpholinyl)methanone;

1-(4-chlorobenzyl)-4-[(4,4-diphenyl-1-piperidinyl)methyl]-N,N-dimethyl-1H-imidazole-5-carboxamide;

1-(4-chlorobenzyl)-4-[(4,4-diphenyl-1-piperidinyl)methyl]-N-(2-methoxyethyl)-1H-imidazole-5-carboxamide;

1-(4-chlorobenzyl)-4-[(4,4-diphenyl-1-piperidinyl)methyl]-N-(4-hydroxycyclohexyl)-1H-imidazole-5-carboxamide;

1-(4-chlorobenzyl)-4-[(4,4-diphenyl-1-piperidinyl)methyl]-N-[1-(hydroxymethyl)propyl]-1H-imidazole-5-carboxamide;

1-(4-chlorobenzyl)-4-[(4,4-diphenyl-1-piperidinyl)methyl]-N-(tetrahydro-2-furanylmethyl)-1H-imidazole-5-carboxamide;

{1-(4-chlorobenzyl)-4-[(4,4-diphenyl-1-piperidinyl)methyl]-1H-imidazol-5-yl}[2-(hydroxymethyl)-1-piperidinyl]methanone;

1-(4-chlorobenzyl)-N-[3-(diethylamino)propyl]-4-[(4,4-diphenyl-1-piperidinyl)methyl]-1H-imidazole-5-carboxamide;

{1-(4-chlorobenzyl)-4-[(4,4-diphenyl-1-piperidinyl)methyl]-1H-imidazol-5-yl}[3-(hydroxymethyl)-1-piperidinyl]methanone;

1-(4-chlorobenzyl)-4-[(4,4-diphenyl-1-piperidinyl)methyl]-N-(2-hydroxyethyl)-1H-imidazole-5-carboxamide;

1-(4-chlorobenzyl)-4-[(4,4-diphenyl-1-piperidinyl)methyl]-N-(2-hydroxyethyl)-N-methyl-1H-imidazole-5-carboxamide;

1-(4-chlorobenzyl)-4-[(4,4-diphenyl-1-piperidinyl)methyl]-N-[3-(1H-imidazol-1-yl)propyl]-1H-imidazole-5-carboxamide;

{1-(4-chlorobenzyl)-4-[(4,4-diphenyl-1-piperidinyl)methyl]-1H-imidazol-5-yl}(1-pyrrolidinyl)methanone;

{1-(4-chlorobenzyl)-4-[(4,4-diphenyl-1-piperidinyl)methyl]-1H-imidazol-5-yl}(3-hydroxy-1-pyrrolidinyl)methanone;

1-[4-({1-(4-chlorobenzyl)-4-[(4,4-diphenyl-1-piperidinyl)methyl]-1H-imidazol-5-yl}carbonyl)-1-piperazinyl]-1-ethanone;

{1-(4-chlorobenzyl)-4-[(4,4-diphenyl-1-piperidinyl)methyl]-1H-imidazol-5-yl}(1-piperidinyl)methanone;

1-(4-chlorobenzyl)-N-[2-(diethylamino)ethyl-4-[(4,4-diphenyl-1-piperidinyl)methyl]-N-(2-hydroxyethyl)-1H-imidazole-5-carboxamide;

1-(4-chlorobenzyl)-4-[(4,4-diphenyl-1-piperidinyl)methyl]-N-[2-(4-morpholinyl)ethyl]-1H-imidazole-5-carboxamide;

1-(4-chlorobenzyl)-4-[(4,4-diphenyl-1-piperidinyl)methyl]-N-ethyl-N-(2-hydroxyethyl)-1H-imidazole-5-carboxamide;

{1-(4-chlorobenzyl)-4-[(4,4-diphenyl-1-piperidinyl)methyl]-1H-imidazol-5-yl}(4-ethyl-1-piperazinyl)methanone;

N-(2-amino-2-oxoethyl)-1-(4-chlorobenzyl)-4-[(4,4-diphenyl-1-piperidinyl)methyl]-1H-imidazole-5-carboxamide;

1-(4-chlorobenzyl)-4-[(4,4-diphenyl-1-piperidinyl)methyl]-N-[2-(1-pyrrolidinyl)ethyl]-1H-imidazole-5-carboxamide;

1-(4-chlorobenzyl)-4-[(4,4-diphenyl-1-piperidinyl)methyl]-N-[2-(1H-imidazol-4-yl)ethyl]-1H-imidazole-5-carboxamide;

1-(4-chlorobenzyl)-4-[(4,4-diphenyl-1-piperidinyl)methyl]-N-methyl-1H-imidazole-5-carboxamide;

1-(4-chlorobenzyl)-N-(2,3-dihydroxypropyl)-4-[(4,4-diphenyl-1-piperidinyl)methyl]-1H-imidazole-5-carboxamide;

1-(4-chlorobenzyl)-4-[(4,4-diphenyl-1-piperidinyl)
methyl]-N-[(1-ethyl-2-pyrrolidinyl)methyl]-1H-
imidazole-5-carboxamide;
ethyl 1-({1-(4-chlorobenzyl)-4-[(4,4-diphenyl-1-
piperidinyl)methyl]-1H-imidazol-5-yl}carbonyl)-4-
piperidinecarboxylate;
ethyl 1-({1-(4-chlorobenzyl)-4-[(4,4-diphenyl-1-
piperidinyl)methyl]-1H-imidazol-5-yl]carbonyl)-3-
piperidinecarboxylate;
methyl 3-[({1-(4-chlorobenzyl)-4-[(4,4-diphenyl-1-
piperidinyl)methyl]-1H-imidazol-5-yl}carbonyl)
amino]propanoate;
methyl 2-[({1-(4-chlorobenzyl)-4-[(4,4-diphenyl-1-
piperidinyl)methyl]-1H-imidazol-5-yl}carbonyl)
amino]acetate;
1-(4-chlorobenzyl)-4-[(4,4-diphenyl-1-piperidinyl)
methyl]-N-(2-pyridinylmethyl)-1H-2-imidazole-5-
carboxamide;
1-(4-chlorobenzyl)-4-[(4,4-diphenyl-1-piperidinyl)
methyl]-N-[2-(2-pyridinyl)ethyl]-1H-imidazole-5-
carboxamide;
1-(4-chlorobenzyl)-4-[(4,4-diphenyl-1-piperidinyl)
methyl]-N-(3-pyridinylmethyl)-1H-imidazole-5-
carboxamide;
1-(4-chlorobenzyl)-4-[(4,4-diphenyl-1-piperidinyl)
methyl]-N-(2-hydroxy-1,1-dimethylethyl)-1H-
imidazole-5-carboxamide;
1-(4-chlorobenzyl)-4-[(4,4-diphenyl-1-piperidinyl)
methyl]-N-(2-hydroxy-1-methylethyl)-1H-imidazole-
5-carboxamide;
1-(4-chlorobenzyl)-4-[(4,4-diphenyl-1-piperidinyl)
methyl]-N-[3-(2-oxo-1-pyrrolidinyl)propyl]-1H-
imidazole-5-carboxamide;
N-[2-(acetylamino)ethyl]-1-(4-chlorobenzyl)-4-[(4,4-
diphenyl-1-piperidinyl)methyl]-1H-imidazole-5-
carboxamide;
1-(4-chlorobenzyl)-4-[(4,4-diphenyl-1-piperidinyl)
methyl]-N-[2-(2-hydroxyethoxy)ethyl]-1H-imidazole-
5-carboxamide;
1-(4-chlorobenzyl)-4-[(4,4-diphenyl-1-piperidinyl)
methyl]-N-[1-(hydroxymethyl)cyclopentyl]-1H-
imidazole-5-carboxamide;
1-(4-chlorobenzyl)-4-[(4,4-diphenyl-1-piperidinyl)
methyl]-N-[2-hydroxy-1-(hydroxymethyl)ethyl]-1H-
imidazole-5-carboxamide;
1-(4-chlorobenzyl)-4-[(4,4-diphenyl-1-piperidinyl)
methyl]-N-(3-methoxypropyl)-1H-imidazole-5-
carboxamide;
1-({1-(4-chlorobenzyl)-4-[(4,4-diphenyl-1-piperidinyl)
methyl]-1H-imidazol-5-yl}carbonyl)-2-
pyrrolidinecarboxamide;
1-({1-(4-chlorobenzyl)-4-[(4,4-diphenyl-1-piperidinyl)
methyl]-1H-imidazol-5-yl}carbonyl)-2-
pyrrolidinecarboxamide;
{1-(4-chlorobenzyl)-4-[(4,4-diphenyl-1-piperidinyl)
methyl]-1H-imidazol-5-yl}[4-(2-hydroxyethyl)-1-
piperidinyl]methanone;
1-(4-chlorobenzyl)-4-[(4,4-diphenyl-1-piperidinyl)
methyl]-N-(2-propynyl)-1H-imidazole-5-
carboxamide;
4-({1-(4-chlorobenzyl)-4-[(4,4-diphenyl-1-piperidinyl)
methyl]-1H-imidazol-5-yl}carbonyl)-2-piperazinone;
1-(4-chlorobenzyl)-4-[(4,4-diphenyl-1-piperidinyl)
methyl]-N-[1-(hydroxymethyl)propyl]-1H-imidazole-
5-carboxamide;
1-{3-(4-chlorobenzyl)-[1,2,4]oxadiazol-5-ylmethyl}4,4-
diphenylpiperidine.

6. A process for the preparation of a compound of formula
(I) as defined in claim 1 which comprises:

(i) when Y represents CH$_2$,
reductive amination of a compound of general formula (II)

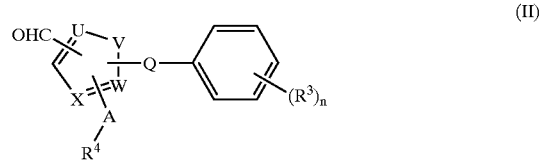

(II)

wherein R$^3$, R$^4$, A, Q, U, V, W, X and n are as defined in
claim 1, with a compound of formula (III)

(III)

wherein R$^1$ and R$^2$ are as defined in claim 1; or (ii) when Y represents C1 to 4 alkyl,
reacting a compound of general formula (IV)

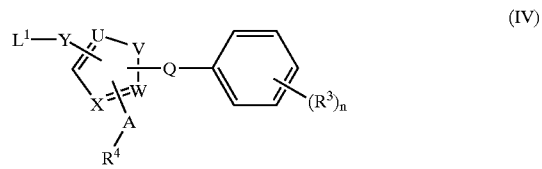

(IV)

wherein R$^3$, R$^4$, A, Q, U, V, W, X and n are as defined in
claim 1 and L is a leaving group,
with a compound of formula (III); or (iii) when Y represents CO,
reacting a compound of general formula (V)

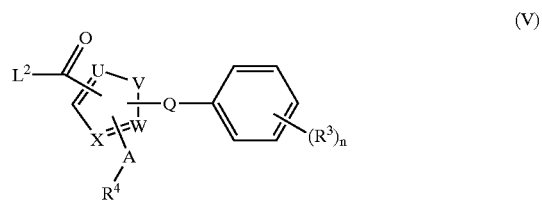

(V)

wherein R$^3$, R$^4$, A, Q, U, V, W, X and n are as defined in
claim 1 and L is a leaving group,
with a compound of formula (III); or (iv) when at least one R$^3$ group in formula (I) represents
optionally substituted C1 to 6 alkoxy,
reacting a compound of formula (VI)

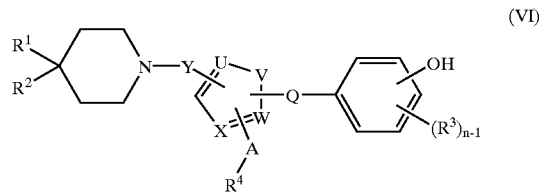

(VI)

wherein $R^1$, $R^2$, $R^3$, $R^4$, A, Q, U, V, W, X, Y and n are as defined in claim 1, with a compound of formula (VII)

     (VII)

wherein R is such that the resultant group OR represents an optionally substituted C1 to 6 alkoxy group as defined for $R^3$ in claim 1, and $L^3$ is a leaving group;

(v) when A represents CO and $R^4$ represents $NR^{10}R^{11}$, reacting a compound of formula (VIII)

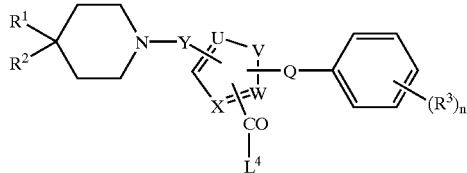     (VIII)

wherein $R^1$, $R^2$, $R^3$, Q, U, V, W, X, Y and n are as defined in claim 1, and L is a leaving group, with a compound of formula (IX)

     (IX)

wherein $R^{10}$ and $R^{11}$ are as defined in claim 1; or (vi) when A represents $CH_2$ and $R^4$ represents $NR^{10}R^{11}$, reductive amination of a compound of formula (X)

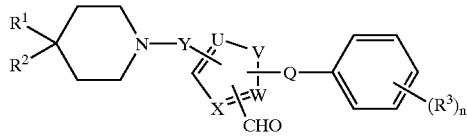     (X)

wherein $R^1$, $R^2$, $R^3$, Q, U, V, W, X, Y and n are as defined in claim 1, with a compound of formula (IX)

     (IX)

wherein $R^{10}$ and $R^{11}$ are as defined in claim 1; or (vii) when Q is bonded to V and V represents nitrogen, reacting a compound of formula (XI)

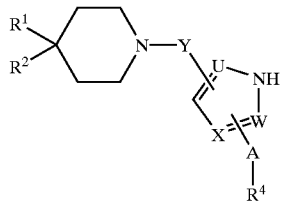     (XI)

wherein $R^1$, $R^2$, $R^3$, A, U, W, X and Y are as defined in claim 1, with a compound of formula (XII)

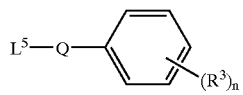     (XII)

wherein $R^3$, Q and n are as defined in claim 1 and $L^5$ is a leaving group; and optionally after (i), (ii), (iii), (iv), (v), (vi) or (vii) converting the compound of formula (I) to a further compound of formula (I) and/or forming a pharmaceutically acceptable salt or solvate of the compound of formula (I).

7. A composition comprising a compound of formula (I), or a pharmaceutically acceptable salt or solvate thereof, as claimed in any one of claims 1 to 5 in association with a pharmaceutically acceptable adjuvant, diluent or carrier.

8. A process for the preparation of a composition as claimed in claim 7 which comprises mixing said compound of formula (I), with a pharmaceutically acceptable adjuvant, diluent or carrier.

9. A method of treating an inflammatory disease in a person suffering from said disease, which comprises administering to the person a therapeutically effective amount of a compound of formula (I), or a pharmaceutically acceptable salt or solvate thereof, as claimed in any one of claims 1 to 5.

10. A method of treating a disease or pathological condition treatable by inhibition of CCR1 and/or CCR3 chemokine receptor activity, said method comprising administering to a person in need thereof an inhibition-effective amount of a compound of formula (I), or a pharmaceutically acceptable salt or solvate thereof, as claimed in any one of claims 1 to 5.

11. A method of treating chronic obstructive pulmonary disease, said method comprising administering to a person in need thereof an effective amount of a compound of formula (I), or a pharmaceutically acceptable salt or solvate thereof, as claimed in any one of claims 1 to 5.

12. A method of treating rheumatoid arthritis, said method comprising administering to a person in need thereof an effective amount of a compound of formula (I), or a pharmaceutically acceptable salt or solvate thereof, as claimed in any one of claims 1 to 5.

* * * * *